United States Patent
Strickland et al.

(10) Patent No.: US 6,179,852 B1
(45) Date of Patent: Jan. 30, 2001

(54) CARPAL TUNNEL DEVICE AND METHOD

(75) Inventors: James W. Strickland, Zionsville; Brian K. Berelsman, Bourbon, both of IN (US)

(73) Assignee: Biomet, Inc., Warsaw, IN (US)

(*) Notice: Under 35 U.S.C. 154(b), the term of this patent shall be extended for 0 days.

(21) Appl. No.: 09/241,818

(22) Filed: Feb. 1, 1999

(51) Int. Cl.$^7$ .................................................. A61B 17/32
(52) U.S. Cl. ........................................ 606/167; 606/185
(58) Field of Search ................................. 606/167, 185, 606/148, 150, 170, 171, 172, 174, 184, 144; 227/180.1, 175.2, 176.1

(56) References Cited

U.S. PATENT DOCUMENTS

| | | |
|---|---|---|
| Re. 35,525 | 6/1997 | Stefanchik et al. . |
| 3,750,671 | 8/1973 | Hedrick . |
| 4,962,770 | 10/1990 | Agee et al. . |
| 5,029,573 | 7/1991 | Chow . |
| 5,273,024 | 12/1993 | Menon et al. . |
| 5,325,883 | 7/1994 | Orr . |
| 5,387,222 | 2/1995 | Strickland . |
| 5,387,223 | 2/1995 | Agee et al. . |
| 5,458,598 | 10/1995 | Feinberg et al. . |
| 5,472,448 | 12/1995 | Marinoff et al. . |
| 5,472,488 | 12/1995 | Marinoff et al. . |
| 5,507,800 * | 4/1996 | Strickland ............ 606/167 |
| 5,578,051 | 11/1996 | Mirza . |
| 5,611,808 | 3/1997 | Hossain et al. . |
| 5,613,976 | 3/1997 | Agee et al. . |
| 5,636,779 * | 6/1997 | Palmer .............. 227/175.2 |
| 5,649,946 | 7/1997 | Bramlet . |
| 5,651,790 | 7/1997 | Resnick et al. . |
| 5,653,713 | 8/1997 | Michelson . |

OTHER PUBLICATIONS

S. L. Carter, "A new instrument: a carpal tunnel knife," *The Journal of Hand Surgery* v. 16, No. 1, pp. 178–179 (Jan. 1991).

"Instruments for endoscopic release of the carpal ligament (1–Portal Technique)," available at www.karlstorz.com/np-carp.htm.

(List continued on next page.)

*Primary Examiner*—Michael Buiz
*Assistant Examiner*—Lien Ngo
(74) *Attorney, Agent, or Firm*—Woodard, Emhardt, Naughton, Moriarty & McNett

(57) ABSTRACT

A carpal tunnel device and method for performing carpal tunnel release surgery is provided. The carpal tunnel device includes a carpal ligament capture clip and a knife, useable therewith. The carpal tunnel capture clip includes a handle, a body portion and upper and lower skids. A central guide channel extends through the body portion of the capture clip. Channels located in the skids are aligned with the central guide channels. Under anesthesia an incision is made in a patient's palm. The carpal ligament capture clip is placed into the palm, facing towards the wrist with the upper and lower skids straddling the transverse carpal ligament. The capture clip is then advanced towards the wrist until the distal ends of the upper and lower skids extend beyond the carpal ligament and the carpal ligament is entrapped between the portions of the skids containing the upper and lower guide channels. At that time the knife blade is introduced through the central guide channel and advanced into the upper and lower guide channels. The knife, bounded by the clip on all sides, is advanced until the transverse carpal ligament is completely divided. The capture clip and knife are removed. The incision is closed and an appropriate dressing is applied.

29 Claims, 25 Drawing Sheets

OTHER PUBLICATIONS

P. C. Innis, "Endoscopic Carpal Tunnel Release," *Journal of the Southern Orthopedic Association* v. 5, No. 4 (Winter 1996), available at http://208.240.93.15/soa/jsoawt96/jsoawt5.htm.

"Extra–Synovial Sub–Fascial Carpal Tunnel Release—A Guide For The Seradge Technique & Instruments," George Tiemann and Company, Hauppauge, New York.

"Distal Single Incision Endoscopic Carpal Tunnel Release System & Technique," A.M. Surgical, Inc., Smithtown, New York.

"GRS™ Carpal Tunnel Release System," RMS Orthopaedic Products.

"Agee Carpal Tunnel Release System".

"Stapling techniques general surgery", 1980 United States Surgery Corporation, p. 42, 2nd edition.*

* cited by examiner

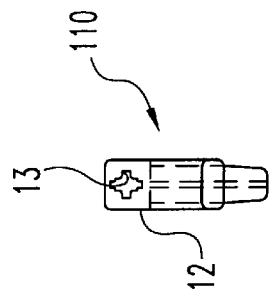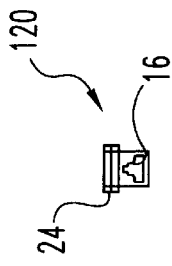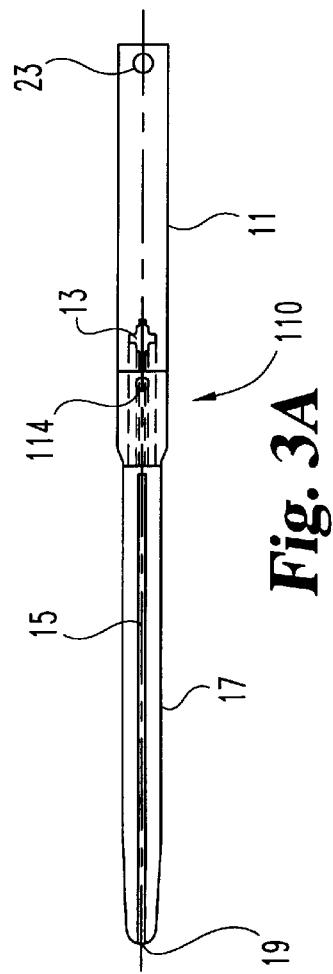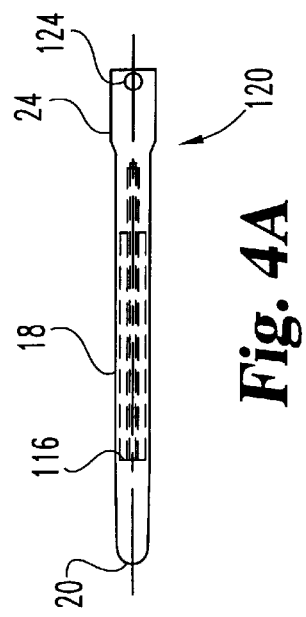

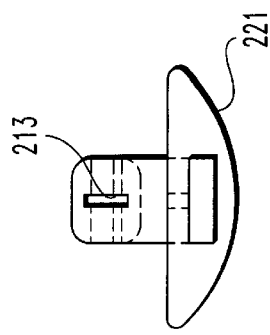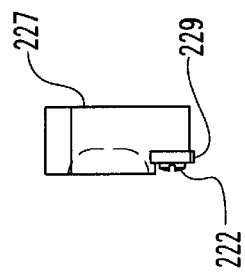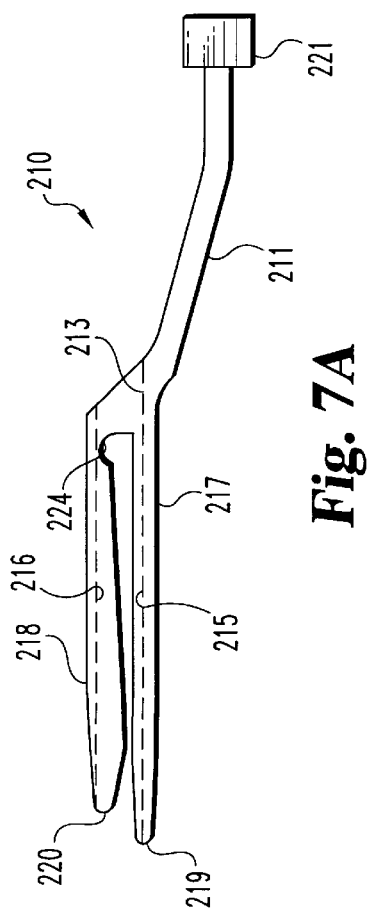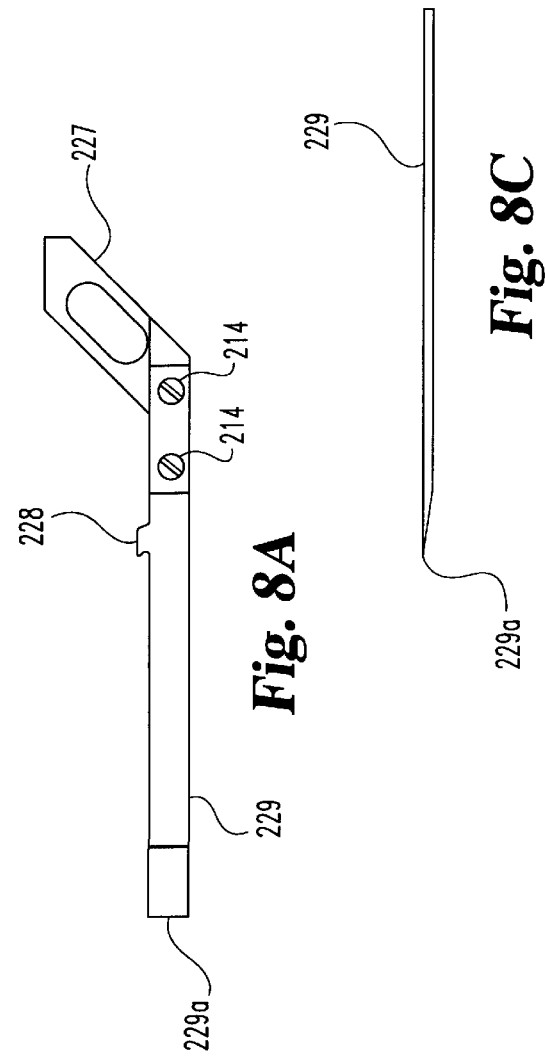

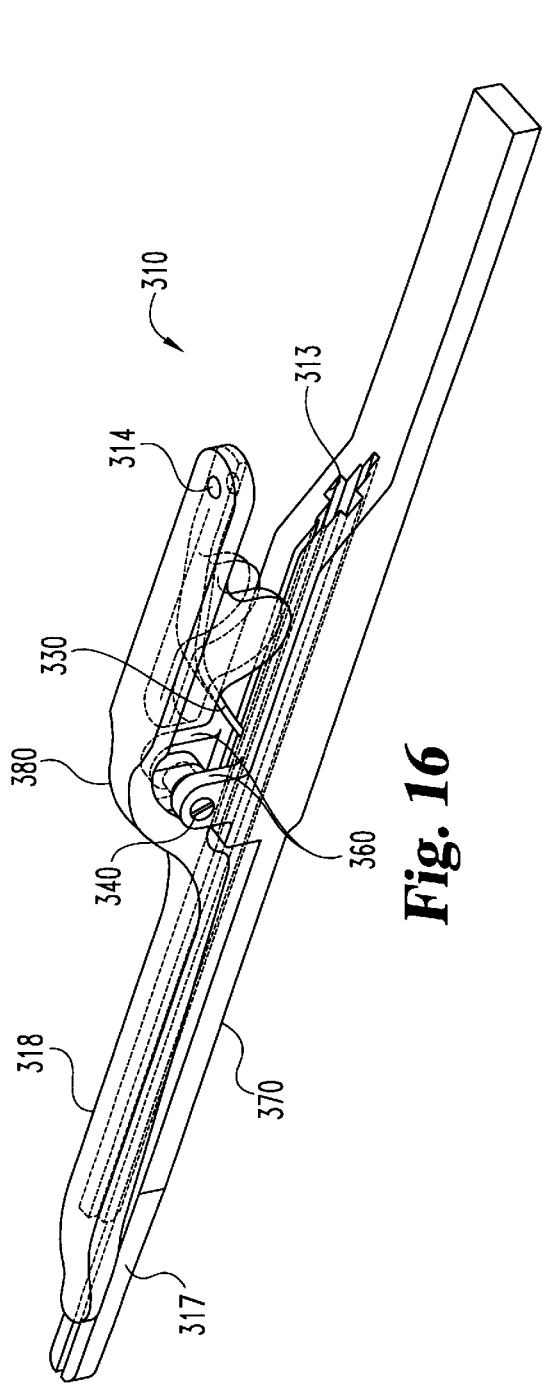
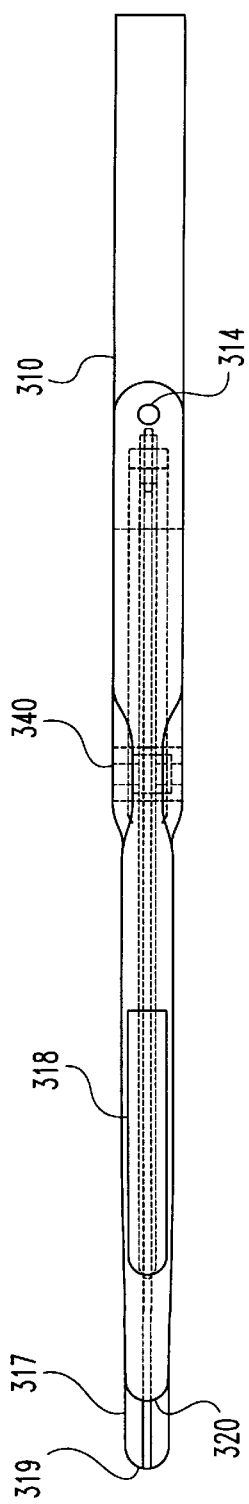

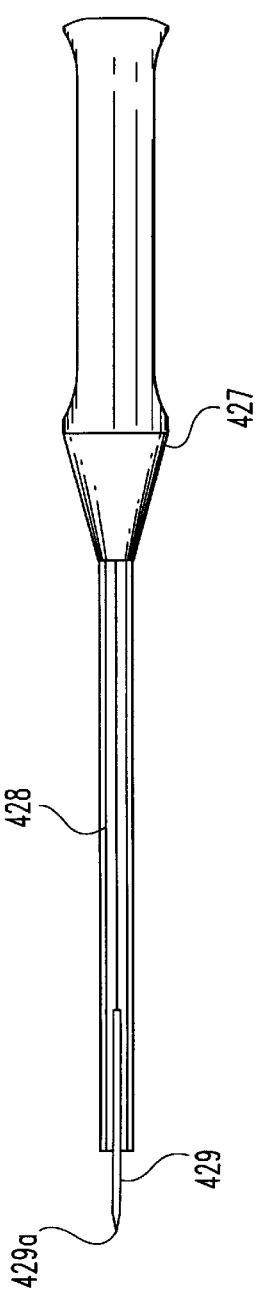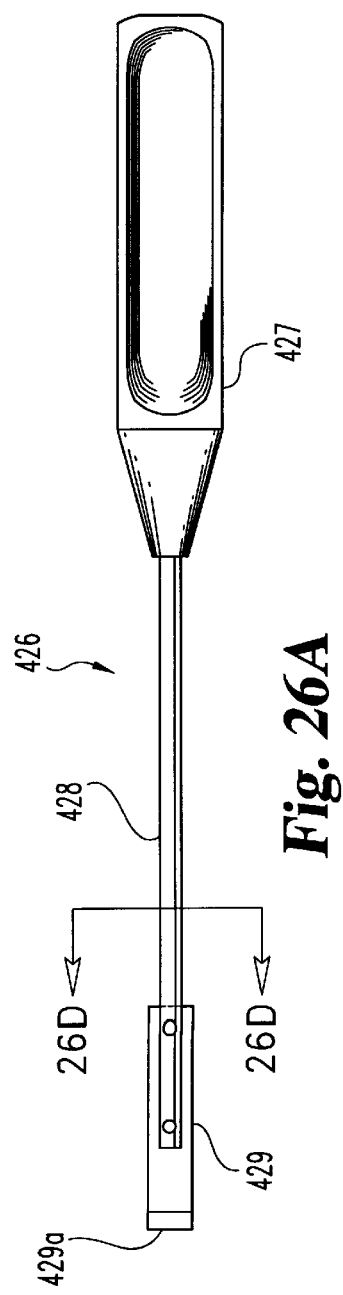

CARPAL TUNNEL DEVICE AND METHOD

BACKGROUND OF THE INVENTION

The present invention relates generally to surgery, and in particular to the use of a carpal tunnel clip and knife device to perform carpal tunnel release surgery.

Surgical decompression of the carpal tunnel, which is often referred to as carpal tunnel release surgery, is the most commonly performed surgical procedure in the United States. The condition is frequent in middle-aged persons whose job requires exposure to vibrating tools or chronic, repetitious use of the hands, such as on keyboards or on assembly lines. Carpal tunnel syndrome is normally characterized by some combination of wrist pain, forearm aching, and/or pain, tingling and numbness in the thumb, index and middle fingers. The pain results from compression of the median nerve in an anatomic passageway in the wrist and palm that is frequently referred to as the carpal tunnel.

Historically, the operative procedure designed to eliminate the symptoms of carpal tunnel syndrome includes making an incision in the palm—sometimes extending across the wrist—to divide the deep transverse carpal ligament and its proximal fascial extension, and release the pressure on the median nerve. Although the procedure has been highly successful in relieving most patients' symptoms, it is often complicated by tenderness around the incision site in the proximal palm and across the wrist. In addition, patients frequently experience "pillar pain" at the base of the thenar and hypothenar eminences, just distal to the wrist crease and on each side of the surgical scar. This post-surgical discomfort has been implicated as the cause for the slow return of patients to occupational activities following conventional carpal tunnel release surgery.

In recent years, there have been efforts made to alter the technique of carpal tunnel release surgery in an effort to minimize the amount of proximal palm and pillar pain, and allow patients to resume normal occupational and domestic activities more quickly. One such method involves making a relatively shorter incision located entirely in the palm and then dividing the deep transverse carpal ligament by straddling the ligament with small blunt scissors which are passed proximally toward the patient's wrist. Although this technique is effective, there is some danger of inadvertent injury to the median nerve or other structures from the tip of the scissors as they are blindly passed in a proximal direction. Further, the length of incision required in order to divide the majority of the ligament prior to scissor passage, may still be large enough to lead to some palmar pain.

The use of one of several endoscopic methods for division of the deep transverse carpal ligament has also received considerable popularity during the past several years. These techniques employ the passage of a special instrument beneath the carpal ligament, such as for example, the method shown in U.S. Pat. No. 5,029,573 to Chow, and then utilize fiberoptics and special cutting instruments to observe and divide the ligament. Although efforts have been made to make these techniques as simple and safe as possible, they still require specialized training and a reasonably long learning curve before the surgeon becomes adept at their use. Complications such as injury to or division of, the median nerve, one of its branches, the tendons within the carpal vault or the superficial arterial arch of the palm have been described with disconcerting frequency. In some reported cases, the instrument has actually been passed into the wrong passageway where injury may occur to the ulnar nerve or artery. Endoscopic carpal tunnel release surgery averages from 30 to 60 minutes for completion and can be done under either a general or local anesthesia. Apart from being a rather lengthy procedure, endoscopic techniques have been challenged as not always being consistent in their ability to completely divide the transverse carpal ligament.

What is needed is a simple, safe and effective technique for division of the deep transverse carpal ligament that requires only a small mid-palmar incision and utilizes an instrument designed to protect adjacent tissues when cutting the ligament.

SUMMARY OF THE INVENTION

It is an object of this invention to provide improved carpal tunnel inventions and methods of using said inventions. More specifically, it is an object to provide a carpal tunnel clip and knife device to produce greater simplicity for division of the transverse carpal ligament during carpal tunnel release surgery, while limiting the possibility of extraneous soft tissue being damaged during knife passage.

It is a further object of this invention to provide an improved method for performing carpal tunnel release surgery.

Further objects, features and advantages of the present inventions shall become apparent from the detailed drawings and descriptions provided herein.

BRIEF DESCRIPTION OF THE DRAWINGS

FIG. 3A is a top view of the body portion of the carpal ligament capture clip of FIG. 2.

FIG. 3B is an end view of the body portion of the carpal ligament capture clip of FIG. 3A.

FIG. 4A is a top view of the capture portion of the carpal ligament capture clip of FIG. 2.

FIG. 4B is an end view of the capture portion of the carpal ligament capture clip of FIG. 4A.

FIG. 7A is a side view of the carpal ligament capture clip of the carpal tunnel device of FIG. 6A.

FIG. 7B is an end view of the carpal ligament capture clip of FIG. 7A.

FIG. 8A is a side view of a knife useful in connection with various embodiments of the present invention.

FIG. 8B is an end view of the knife of FIG. 8A.

FIG. 8c is a bottom view of the blade portion of the knife of FIG. 8A.

FIG. 16 is an upper, right perspective view of a carpal ligament capture clip of the carpal tunnel device of FIG. 15.

FIG. 17 is a top view of the carpal ligament capture clip of FIG. 16.

FIG. 26A is a side view of a knife useful in connection with some embodiments of the present invention.

FIG. 26B is a top view of the knife shown in FIG. 26A.

FIG. 26C is an end view of the knife shown in FIG. 26A.

FIG. 26D is a cross section taken through the knife stem looking in the direction of arrows 26D—26D of FIG. 26A.

DESCRIPTION OF PREFERRED EMBODIMENTS

For the purposes of promoting an understanding of the principles of the invention, reference will now be made to the embodiments illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

Figure 1:
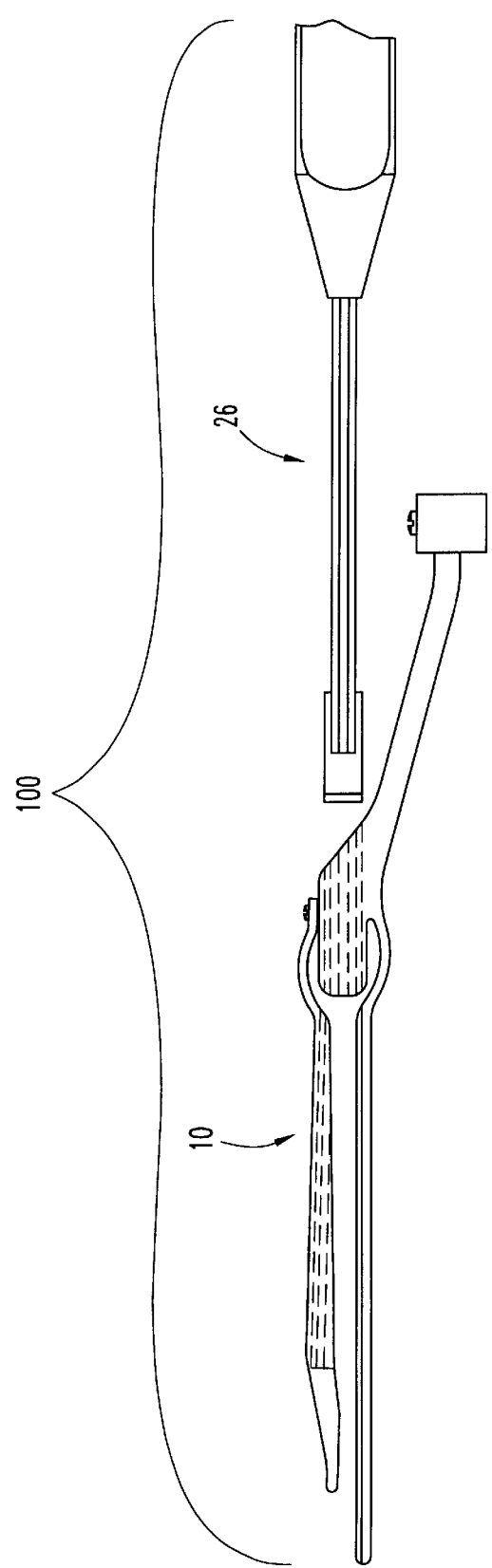
FIG. 1 is a side view of a carpal tunnel device in accordance with one embodiment of the present inventions.

In FIG. 1 there is shown an improved carpal tunnel device in accordance with one embodiment of the present invention. The carpal tunnel device 100 includes a carpal ligament capture clip or sheath 10 and a knife 26. The carpal ligament capture clip 10 may be made out of spring steel, stainless steel, plastic, or any combination of the three. Additionally, portions of the knife 26 may be made from stainless steel. In use, the knife 26 is slidably engaged through the central guide channel of the capture clip 10, to sever the transverse carpal ligament entrapped in the clip 10.

Figure 2:
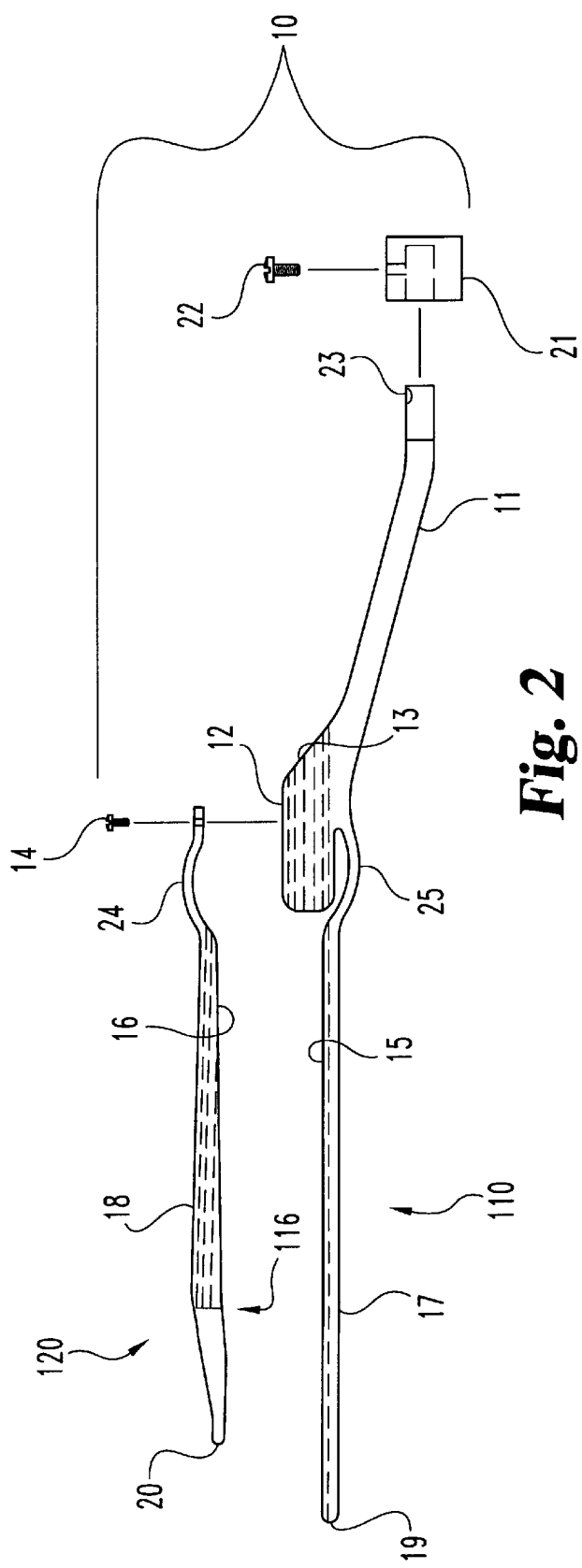
FIG. 2 is an exploded side view of a carpal ligament capture clip of the carpal tunnel device of FIG. 1.

Referring now to FIG. 2, there is shown an exploded view of the carpal ligament capture clip 10 of FIG. 1. The carpal ligament capture clip 10 comprises a guide portion 110 and a capture arm 120. The guide portion 110 of the carpal ligament capture clip 10 includes a handle portion 11, a body portion 12 and a lower skid portion 17. In the present embodiment, the handle portion 11 is contoured downward (in use, towards the palm) and includes a flattened "T" extension or extension cross-piece 21 that assures its rotatory stability. The extension cross-piece 21 includes a threaded hole for receipt of a screw 22. Handle 11 additionally includes a threaded hole 23 to lockingly engage the screw 22 when the cross-piece 21 is slid onto the handle 11. Alternatively the handle 11 and cross-piece 21 may be made as a single piece, or may be omitted if desired.

Referring to FIGS. 2, 3A and 3B, The body portion 12 of the guide portion includes a central guide channel 13, therethrough to receive the blade and shaft of knife 26. The cross-sectional shape of central guide channel 13 is preferably adapted to closely fit the cross-sectional shape of the shaft of the knife 26, and additionally provides clearance in the body portion 12 for the blade. In the present embodiment, as shown in FIGS. 5A–5D, the cross-sectional shape of knife 26 is cross shaped. This is not meant to be limiting, as other desired shaft cross sections may be used. See for example, FIGS. 8A–8C and 26A–26D. Similarly, shafts having circular or other geometric cross-sections may be used.

The lower skid 17 includes a blunted tip 19, and a lower guide channel 15 aligned with the central guide channel 13 of the body portion 12. The lower guide channel 15 may, optionally extend the entire length of the lower skid 17, as shown, or may, alternatively extend for only a portion of the lower skid, as described below in connection with the upper skid. Additionally, depthwise, the lower guide channel 15 extends through only a portion of the skid, thus the blade of the knife 26 is not exposed to tissue below the lower skid 17. The lower guide channel 15 can have a cross-sectional shape adapted to receive the lower portion of the blade or the lower portion of the blade along with a portion of the knife shaft, if desired. FIG. 3A is a top view of the guide portion 110 of the carpal ligament capture clip 10, without the cross-piece 21. FIG. 3B is an end view of the guide portion of FIG. 3A. As can be seen more particularly in FIG. 3A, the body portion 12 includes a threaded hole 114 for engaging the screw 14 of FIG. 2. Screw 14 may be replaced by any appropriate type of fastener, rivet, bolt, etc., or may be omitted entirely and the upper skid may be soldered or welded to the body 12.

Referring now to FIGS. 2, 4A and 4B, FIG. 4A is a top view of the capture arm 120 of the carpal ligament capture clip 10. The capture arm 120 includes an upper skid 18. Upper skid 18 includes a blunt tip 20 and an upperguide channel 16 aligned with the central guide channel 13 of the body 12. As with the lower guide channel 15 of the guide portion 110, the upper guide channel 16 of the upper skid 18 may be adapted to have the desired cross-sectional shape of the upper portion of the blade or the upper portion of the blade along with a portion of the knife shaft, if desired, so as to align the knife when slid through the passage of central guide channel 13 and along the extended guide channel formed in the upper and lower skids. Additionally, depthwise, the upper guide channel 16 extends through only a portion of the skid, thus the blade of the knife 26 is not exposed to tissue above the upper skid 18. The total combined length of the central guide channel 13 and the upper guide channel 16 should be greater than at least 3 cm, to ensure that the entire carpal ligament is cut prior to the knife blade encountering the end of the upper guide channel 16. The capture arm 120 additionally includes a hole 124 therethrough to allow screw 14 to pass.

The transverse carpal ligament has a changing width. For example, the typical carpal tunnel ligament is 1 mm in width proximal to the wrist and 3 mm in width distal from the wrist (proximal to the palm area). The upper and lower skids 18 and 17 of the carpal ligament capture clip 10 are designed to straddle the transverse carpal ligament and, as described more fully below, be passed from the (distal) palm to the (proximal) wrist along the entire length of the ligament in preparation for ligamental division.

Optionally in the present embodiment, as shown in FIGS. 1–4B, the lower skid 17 of the carpal ligament capture clip 10 is designed to extend beyond the tip 20 of the upper skid 18. For example, in one embodiment of the present invention, the length of the upper skid excluding the portion where the skid is over the body, is about 2.2 inches in length, whereas, in the same embodiment the lower skid was chosen to be about 2.5 inches in length. This permits visual confirmation of the correct positioning of the carpal ligament capture clip 10 through direct observation in the wound.

Additionally, as shown in FIGS. 1–4B, the opposing inside surfaces of skids 17 and 18 are relatively smooth to permit the carpal ligament to slide between the two skids when the device is introduced into the palm. The term "relatively smooth" used herein is not meant to exclude an unpolished surface, or even a purposely roughened surface, but is meant to exclude a surface including purposeful obstructions, such as teeth, or other similar obstructions which would substantially impede the carpal ligament from sliding over the surface of the skids when in use.

Figure 29:
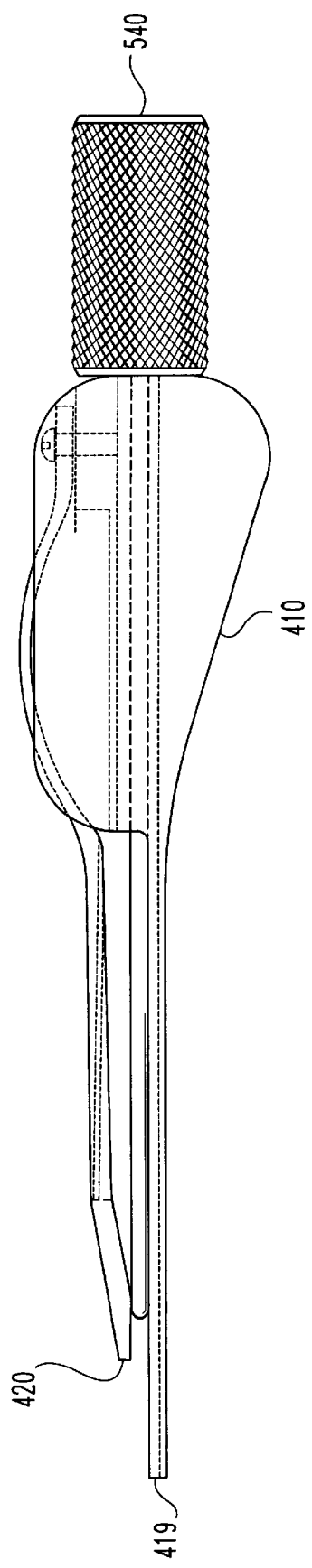
FIG. 29 is a side view of a carpal ligament capture clip including an obturator.

To aid in conforming to the changing width of the carpal ligament, the upper skid 18 is about 2 mm thicker at the distal end of the upper guide channel 16 (proximal to tip 20, and to the wrist end of the carpal ligament when in use), than at the proximal end of the upper guide channel 16 (proximal to the palmar portion of the carpal ligament when in use). For all embodiments herein, the lower skid is preferably of uniform thickness, but optionally may vary in thickness, if desired. Thus the clip will closely adapt to the narrowing width of the transverse carpal ligament as it is passed from the palm to the wrist. At rest, there may be a slight separation between the tips 19 and 20 of the lower and upper skids 17 and 18 to permit the transverse carpal ligament to be initially straddled by the upper and lower skids when first placing the device. Alternatively, the capture clip 10 may be normally biased closed at tips 19 and 20 to keep tissue, other than the carpal ligament, from getting in between the skids during insertion and an obturator or other tool may be used to bias the tips 19 and 20 apart during insertion, such as is shown in FIG. 29 in connection with the embodiment of FIG. 22.

To assure compliance of both skids to the ligament as the instrument is passed from the palm to the wrist, the clip will be capable of slight "spring" separation so that, as the instrument is passed, the distance between the two skids will initially widen but will progressively narrow and continuously grasp the transverse carpal ligament as it becomes thinner. In the embodiment of FIGS. 1–4B, both the guide portion 110 and the capture arm 120 include flexible spring portions 24 and 25, respectively, to allow the skid portions to permit the above described spring separation. Because of the close conformance of the instrument to the ligament, there should be no possibility of extraneous soft tissue entering between the skids where they might be damaged during knife passage.

Figure 5A:
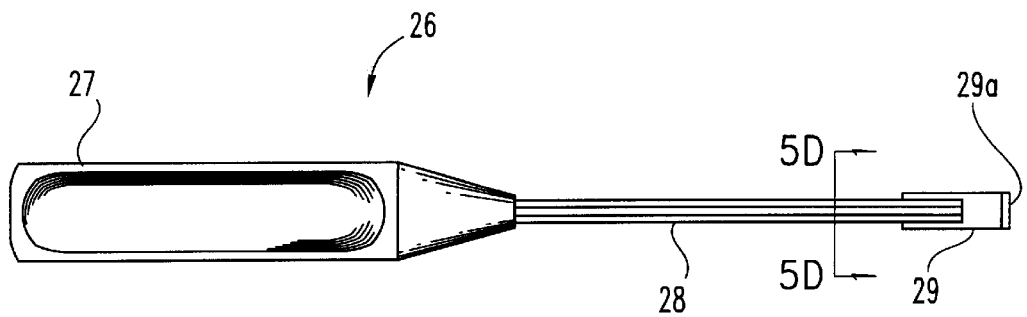
FIG. 5A is a side view of a knife useful in connection with at least some embodiments of the present invention.
Figure 5B:
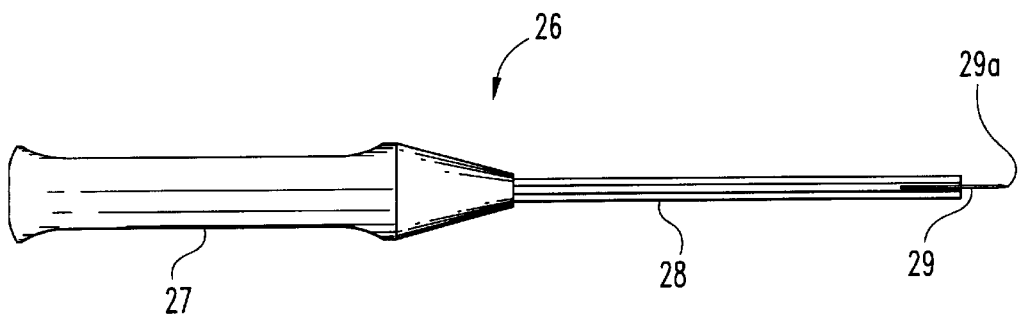
FIG. 5B is a top view of the knife shown in FIG. 5A.
Figure 5C:
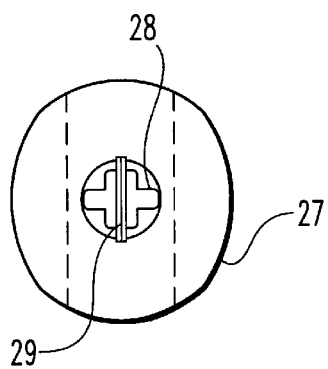
FIG. 5C is an end view of the knife shown in FIG. 5A.
Figure 5D:
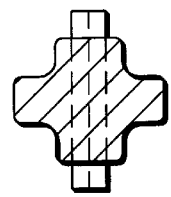
FIG. 5D is a cross section taken through the knife stem looking in the direction of arrows 5D—5D of FIG. 5A.
Figure 6A:
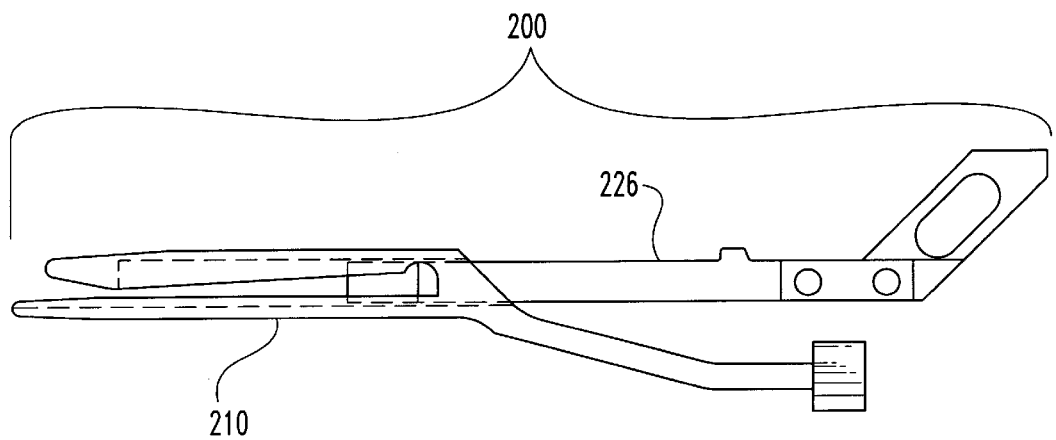
FIG. 6A is a side view of a carpal tunnel device in accordance with another embodiment of the present invention.
Figure 6B:
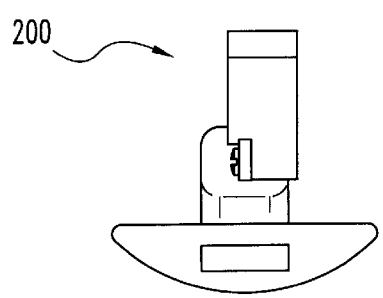
FIG. 6B is an end view of the carpal tunnel device of FIG. 6A.

Referring now to FIGS. 5A–5D, there is shown one possible embodiment of a knife for use with the present invention. Knife 26 includes a handle 27, a shaft 28 and a blade 29. The handle 27 may be contoured, as shown or in any other desired manner, to provide for easy gripping of the tool. Alternatively, the handle 27 may be omitted entirely, if desired. Connected to the handle 27 is the proximal end of the shaft 28. The shaft 28 of the knife 26, of the present embodiment, has a cross-sectional shape of a cross, as can be seen in FIGS. 5C and 5D. As noted above, other geometrical cross-sectional shapes for the shaft may be used, as desired. Attached to the distal end of the shaft 28 is the blade 29.

The height of blade 29 was chosen to be greater than the diameter of the shaft 28, such that blade 29 extends above and below the shaft an equal amount, as shown in FIGS. 5A, 5C and 5D. The distal end of blade 29 includes the cutting edge 29a. It is intended that during use the cutting edge 29a will be maintained substantially perpendicular to the inner surfaces of the upper and lower skids so as to transect the carpal ligament gripped therebetween.

As noted above, preferably the cross-sectional shape of central guide channel 13 is sized to conform to the cross-sectional shape of the shaft, while permitting additional clearance in the top and bottom portions (and not side to side portions) of the central guide channel for the blade 29. This insures that the insertion and use of the knife 26 with the carpal ligament capture clip 10 has a minimum of knife instability and additionally ensures that the knife can be inserted into the central guide channel 13 in only one direction, with the blade 29 perpendicular to the carpal ligament.

Additionally, as the blade 29 and shaft 28 extend into the extended guide channels of the skids, in use, a progressive amount of the knife blade will be covered by the upper skid, thus the knife will only cut the narrowing ligament with no risk of damage to adjacent tissues. The upper and lower guide channels further stabilize and guide the knife through the device. In the present embodiment, at a point 116 before the distal tip 20 of the upper skid 18, the upper guide channel 16 ends. In one particular embodiment where the upper skid is about 2.2 inches in length and the lower skid was chosen to be about 2.5 inches, the guide channel in the upper skid ends more than 0.5 inch from the tip of the upper skid. This serves to stop the passage of the knife blade at the termination of the upper guide channel 16, thus not permitting the knife blade 29 to exit the clip, or even to travel the full length of the bottom skid 17.

Referring now to FIGS. 6A–8C, there is shown a carpal tunnel device 200, in accordance with an embodiment of the present invention. As with the carpal tunnel device of FIGS. 1–4B, the carpal tunnel device 200 includes a capture clip 210 and a knife 226. Similarly, the carpal ligament capture clip 210 includes a handle portion 211 including a flattened "T" extension 221, and a body portion including a passage or channel 213 therethrough. Additionally, the capture clip 210 includes an upper skid 218 and a lower skid 217. The central guide channel 213 through the body portion extends to the upper guide channel 216 in the upper skid 218 and to the lower guide channel 215 in the lower skid 217.

In the present embodiment, the handle 211 and the body portion, including the skids 217 and 218 are integrally formed or are machined from a single piece of spring or stainless steel, but could additionally be made of plastic or a like material. If spring steel is used, an appropriate coating may be provided to protect the device during autoclaving.

As with the embodiment of FIGS. 1–4B, the upper skid 218 is preferably about 2 mm thicker near the distal end of the upper guide channel 216 (proximal to tip 220, and to the wrist end of the carpal ligament when in use), than at the proximal end of the upper guide channel 216 (proximal to the palmar portion of the carpal ligament when in use). For example, in one embodiment of the present invention, the upper skid thickness near the distal end of the upper guide channel 216 is 4 mm in thickness, while at the proximal end of the skid, near the guide body, the skid is 2 mm in thickness. Likewise, as above described, there is normally a slight separation between the tips of the upper and lower skids to permit the skids to initially permit the transverse carpal ligament to be straddled by the capture clip 210 when first placed in the carpal tunnel. In one embodiment, the separation is 1 mm. Alternatively, as described above, the skids may be normally biased closed, but separated slightly by an obturator or other tool during insertion, such as is shown in FIG. 29 in connection with the embodiment of FIG. 22. To assure compliance of both skids to the ligament as the instrument is passed from the palm to the wrist, the clip will be capable of slight "spring" separation so that, as the instrument is passed, the distance between the two skids will initially be widened but will progressively narrow and continuously grasp the transverse carpal ligament as it becomes thinner. As such, the capture clip 210 includes as a portion of the upper skid 218, a cut away "spring" portion 224 to permit the upper skid to bend as needed when first sliding the clip over the thickest, proximal portion of the ligament. Further, as described above in connection with the embodiment of FIGS. 1–4B, the opposing inside surfaces of skids 217 and 218 are relatively smooth to permit the carpal ligament to slide between the two skids when the device is introduced into the palm.

In the embodiment of FIGS. 6A–8C, the shaft portion of the knife 226 is shown as being rectangular in cross section, but a different geometrical cross-section may be chosen, if desired. In the present embodiment, the shaft is shown as being integral with the blade. To correspond to the blade and shaft, the central guide channel 213 is additionally rectangular in cross section. In one embodiment of the present invention, the central guide channel 213 is chosen to be just over 4 mm in height. The knife 226 may include a handle 227 connected to the shaft portion of the blade 229 using screws 214. Additionally, the knife 226 includes a sharpened edge 229a and a stop 228. The stop 228 will abut the body portion of the capture clip 210 when the knife 226 is fully inserted into the capture clip, thus preventing the inadvertent passage of the knife beyond the confines of the clip 210. In embodiments using a knife including a stop, such as stop 228, the upper guide channel 216 may be permitted to extend to the tip 220 of the upper skid 218. Additionally, the stop 228 may be placed such that the blade edge 229a is aligned with the thickest portion of the skid, near the tip 220 when the stop 228 abuts the body of the device.

Figure 15:
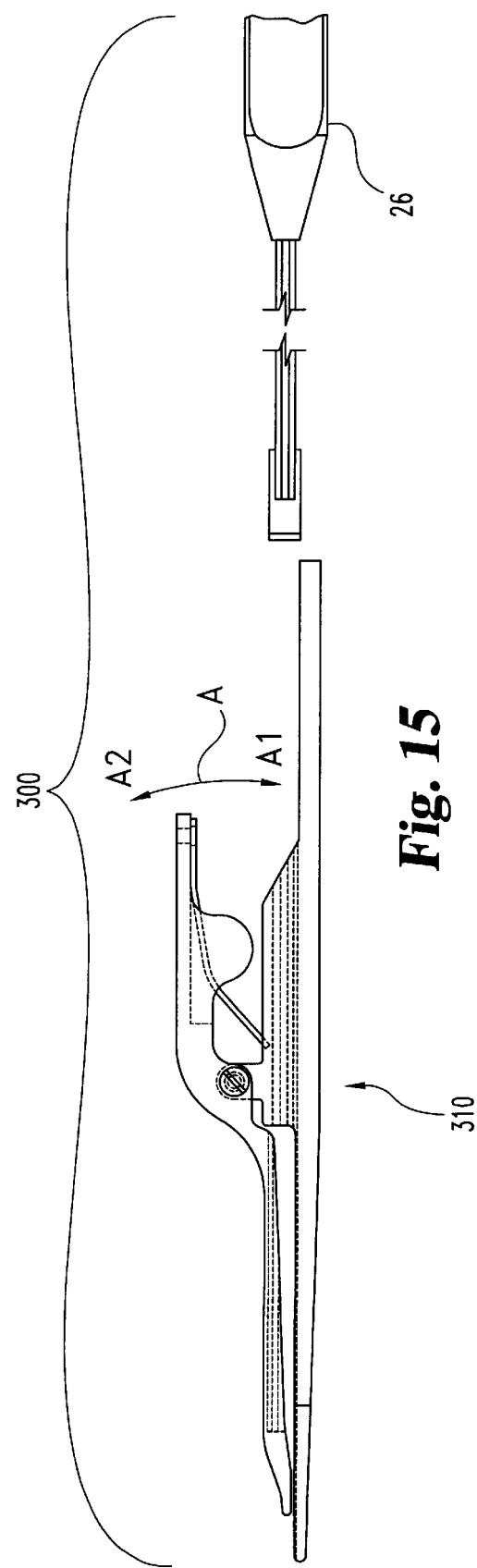
FIG. 15 is a side view of a carpal tunnel device in accordance with one embodiment of the present inventions.

Referring now to FIG. 15 there is shown a carpal tunnel device 300 in accordance with an embodiment of the present invention. The carpal tunnel device 300 comprises a carpal ligament clip 310 and a knife, such as knife 26 of FIGS. 5A–5D. Additionally, as described above in connection with FIGS. 5A–5D, the carpal ligament clip 310 can be adapted to work with knives having other shaft geometries.

Referring now to FIGS. 16–19C, there is shown a carpal ligament capture clip 310. The carpal ligament capture clip 310 comprises a guide portion 370 and a capture arm 380, connected via a shoulder bolt 340. Although a shoulder bolt 340 is shown, this is not intended to be limiting, as it is understood that the capture arm 380 could be connected to the guide portion 370 using any kind of shaft, rod, bolt, pin, ferrule, rivet or similar structure which would permit the capture arm to pivot relative to the guide body. The skids 317 and 318 of the guide portion 370 and the capture arm 380 are normally biased into a closed position by the spring element 330. As shown in FIGS. 20A and 20B, the spring element 330 may be a flat spring made of a thin flexible piece of metal. Alternatively, other types of spring mechanisms may be used to provide a spring bias to the capture arm. In the present embodiment the spring element 330 includes an aperture 332 and a tongue 334. The spring element 330 is connected to the capture arm 380 via a rivet, bolt, pin or similar structure, such as by rivet 314, which passes through the aperture 332 and is biased with respect to the guide portion by the placement of the spring element tongue 334 into an aperture 336 (of FIG. 19B) in the guide portion 370. Alternatively, the aperture 336 may be omitted and the upper portion of the guide channel 313 may be left open along its length. In that case, the spring element tongue 334 would be used to center the spring element 330 in the central guide channel and the shoulders 360 would limit the travel of the spring element 330.

Referring back to FIG. 15, there is shown a directional arrow A. The spring element length and/or the distance of the aperture 336 from the rivet 314 is chosen to cause the spring element 330 to normally bias the capture arm handle 321 in the direction A2 of the arrow A. When a force is applied to the capture arm handle in the direction of arrow A1, the spring element will be biased downward, and the skids 317 and 318 will separate, thus permitting the carpal ligament to pass between them. Releasing the pressure on the capture arm handle 321 will allow the spring element 330 to return to its normally biased position, thus moving the capture arm handle 321 in the direction of arrow A2, and permitting the skids 317 and 318 to close with the carpal ligament trapped between them.

The guide body 370 includes a central guide channel 313 sized to receive a knife blade and shaft therethrough. The central guide channel 313 is aligned, in use, with upper and lower 316 and 315 guide channels in the lower and upper skids 317 and 318 to guide the knife blade along the skids, for severing of the carpal ligament. The guide channels in the lower and upper skids, depthwise, do not extend all the way through the skid. Thus tissue above and below the capture clip is protected from the blade 29.

Figure 18C:
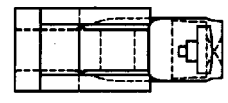
FIG. 18C is an end view of the capture portion of FIG. 18A
Figure 18B:
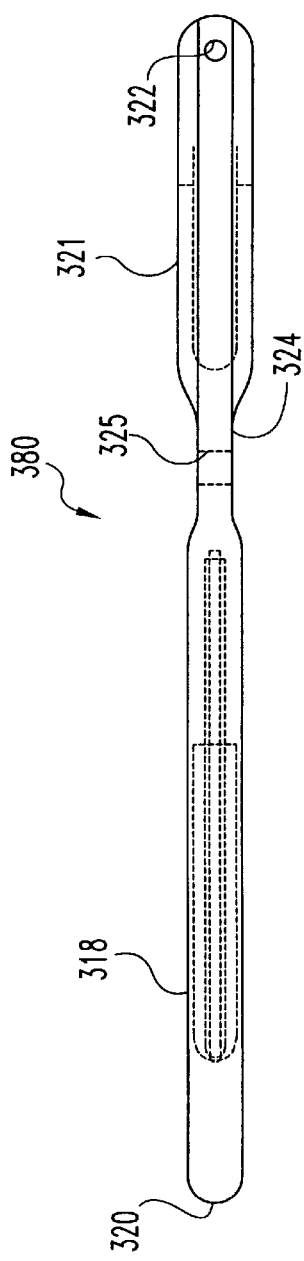
FIG. 18B is a top view of the capture portion of FIG. 18A.
Figure 18A:
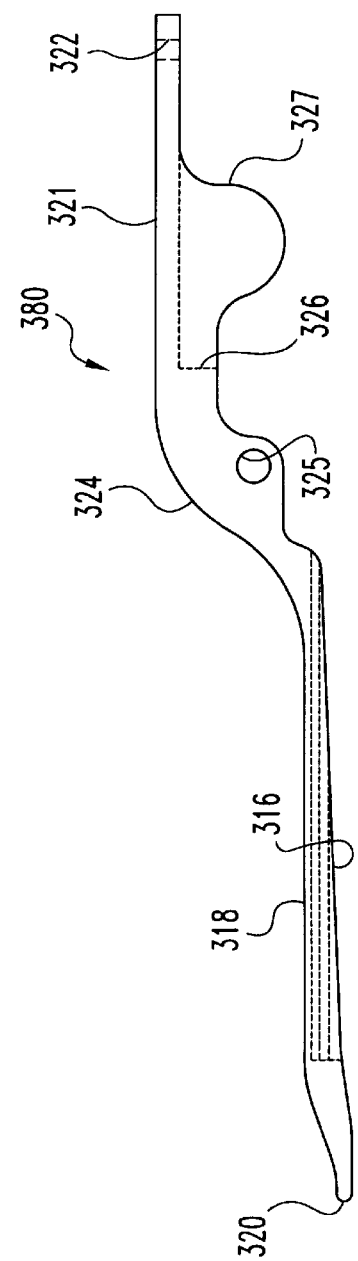
FIG. 18A is a side view of the capture portion of the carpal ligament capture clip of FIG. 16.

Referring more specifically to FIGS. 18A–18C there is shown the capture arm 380 of the carpal ligament capture clip 310. The capture arm includes a capture arm handle 321, a waist portion 324 and the upper skid 318. The capture arm handle 321 includes a hole 322 therethrough for receiving the rivet 314 of FIG. 16. Additionally, the handle includes an additional set of shoulders 327 which serves as a stop limiter, in use, to prevent the clip from being opened greater than a predetermined amount. In use, the shoulders contact the guide body when the clip is opened a predetermined amount and do not permit the spring element to be bent any further. Additionally, there is a cavity 326 formed in the capture arm handle 321, between the shoulders 327, to provide clearance for the spring element 330 of FIGS. 15–16.

The waist portion 324 includes a bore 325 therethrough. The waist portion is designed to fit between the shoulders 360 of the guide portion 370 of the capture clip 310. The bore is sized to receive a shoulder bolt 340 to pivotally connect the capture arm 380 with the guide body 370. As stated above, the capture arm skid 318 includes a guide channel 316 formed therein, which, when assembled with the guide body 370, is aligned with and has the contour of the upper portion of the central guide channel 313. Additionally, as in the examples above, the capture arm is optionally, about 2 mm thicker at the distal end (the end towards tip 320) of the upper skid 318 than at the end of the guide channel 316 to accommodate the narrower width of the carpal ligament at that location. As above, the guide channel 316 ends prior to the ending point of the upper skid 318 to prevent the blade 29 of the knife 26 from passing outside the carpal tunnel clip when the blade edge has reached the end of the channel 316.

Figure 19C:
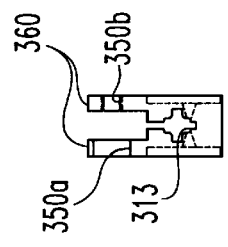
FIG. 19C is a cross section taken through the body portion looking in the direction of arrows 19C—19C of FIG. 19A.
Figure 19B:
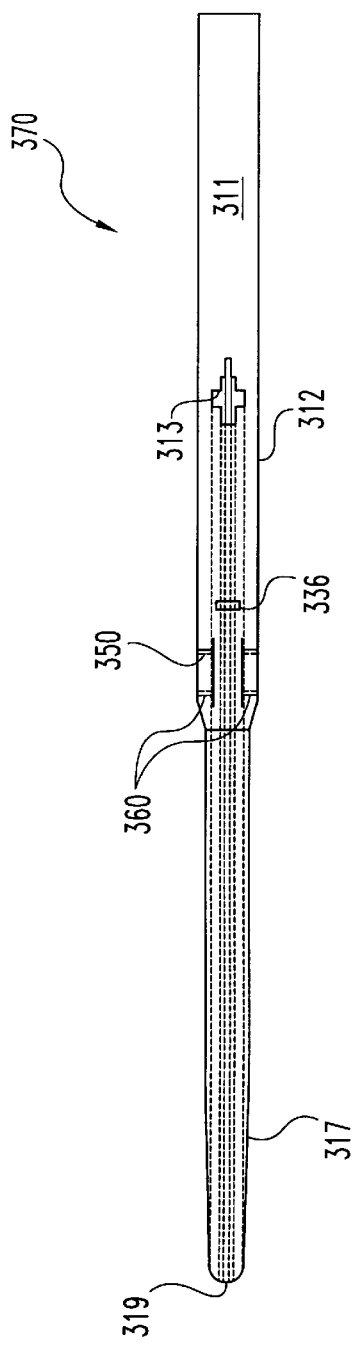
FIG. 19B is a top view of the body portion of the carpal ligament capture clip of FIG. 19A.
Figure 19A:
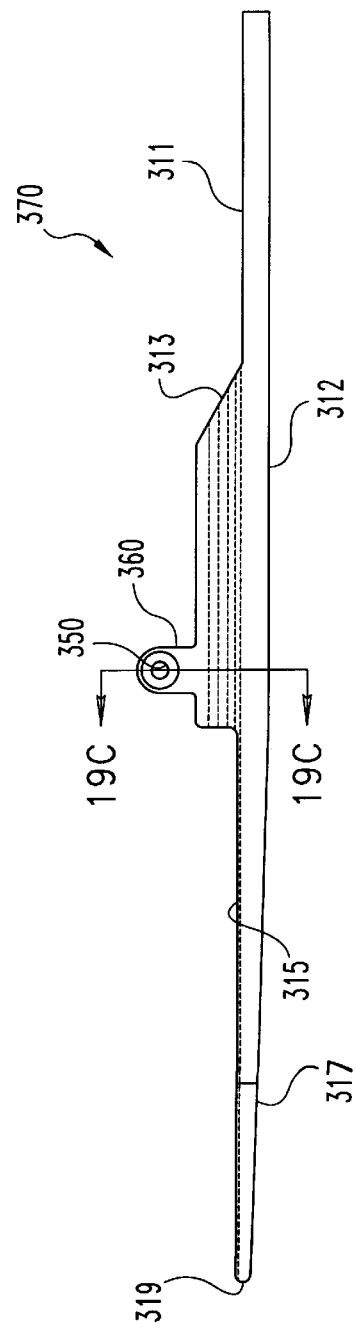
FIG. 19A is a side view of the body portion of the carpal ligament capture clip of FIG. 16.
Figure 20A:
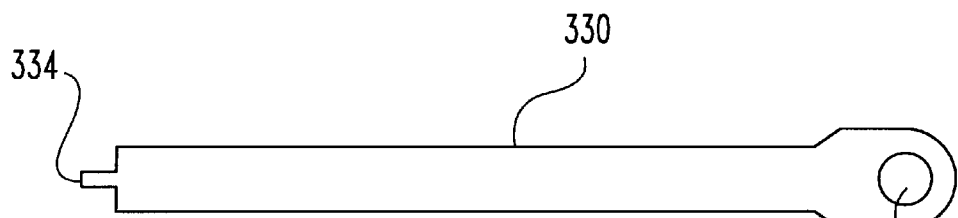
FIG. 20A is an enlarged top view of a spring which may be used with one embodiment of the present inventions.
Figure 20B:
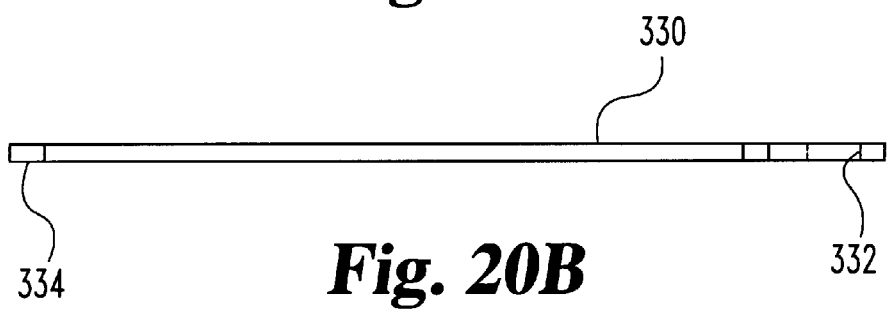
FIG. 20B is an enlarged side view of the spring of FIG. 20A.

Referring now to FIGS. 19A–19C, the carpal ligament capture clip guide body 370 which includes a handle portion 311. The handle portion 311 may be flat and in the same plane as the guide body 370, as shown, or may be contoured as with the handle of carpal ligament capture clips 10 and 210, to conform to the palm in use. Additionally, as with the capture clips 10 and 210, the handle 311 of the capture clip 310 could optionally include a cross piece (not shown).

The guide body 370 additionally includes a body portion 312 having a central guide channel 313 therethrough. The cross-sectional shape of the central guide channel is chosen to conform with the chosen cross-sectional shape of the shaft of the knife chosen, while permitting clearance for the blade in a direction perpendicular to the carpal ligament, thus permitting the knife blade edge to be introduced perpendicular to the ligament. In the present embodiment, the cross-sectional shape of the central guide channel 313 is chosen to be cross shaped, wherein the top and bottom arms of the cross include additional clearance for the greater height of the knife blade. A knife, such as any of the knives of of FIGS. 5A–5D, 8A–8C, or 26A–26D, may be used, or another knife having another cross-sectional shaft geometry may be chosen. Additionally, the central guide channel may preferably be adapted to the shaft geometry for greater stability, as described herein.

Figure 21A:
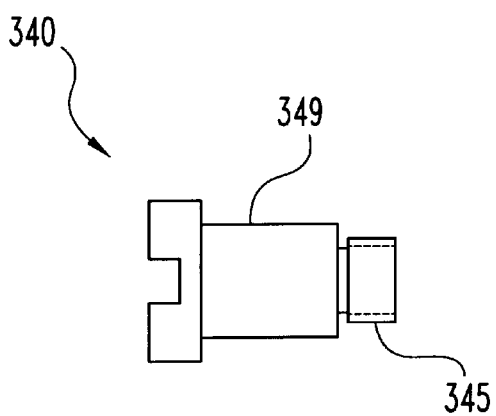
FIG. 21A is an enlarged side view of a shoulder bolt which may be used with one embodiment of the present inventions.
Figure 21B:
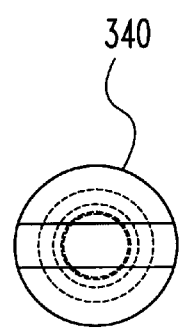
FIG. 21B is an end view of the shoulder bolt of FIG. 21A.

The body portion additionally includes shoulders 360 for supporting the upper capture arm 380 of the capture clip 310. A bore 350 is provided through shoulders 360 to receive the shoulder bolt 340. As shown in FIGS. 19C and 21A, the shoulder bolt 340 includes a stepped body portion 349 including an unthreaded shoulder portion adapted to fit through the bore 350a (FIG. 19C), as well as a narrowed, threaded portion adapted to fit with threads 350b. The shoulder bolt 340 is secured using threads 345.

The lower skid 317 is integral to the body 312, and includes a guide channel 315 formed therein. The guide channel 315 is aligned with and has a cross-sectional shape reflecting the bottom portion of the central guide channel 313 (and correspondingly, the blade and possibly, the shaft cross-section, if desired), so that the passage of the knife 26 will continue through the central guide channel and along the lower skid 317. As described above, in the present embodiment, the lower skid may optionally be made longer than the upper skid to aid in visually determining that the clip is correctly placed before introducing the knife 26 into the central guide channel 313.

Referring now to FIGS. 22–26D, there is shown an improved carpal tunnel device in accordance with another embodiment of the present invention. The carpal tunnel device 400 includes a carpal ligament capture clip or sheath 410 and a knife 426. As with the previous embodiments described, the carpal ligament capture clip 410, may be made out of spring steel, stainless steel, plastic, or any combination of the three. Additionally, portions of the knife 426 may be made from stainless steel.

Figure 22:
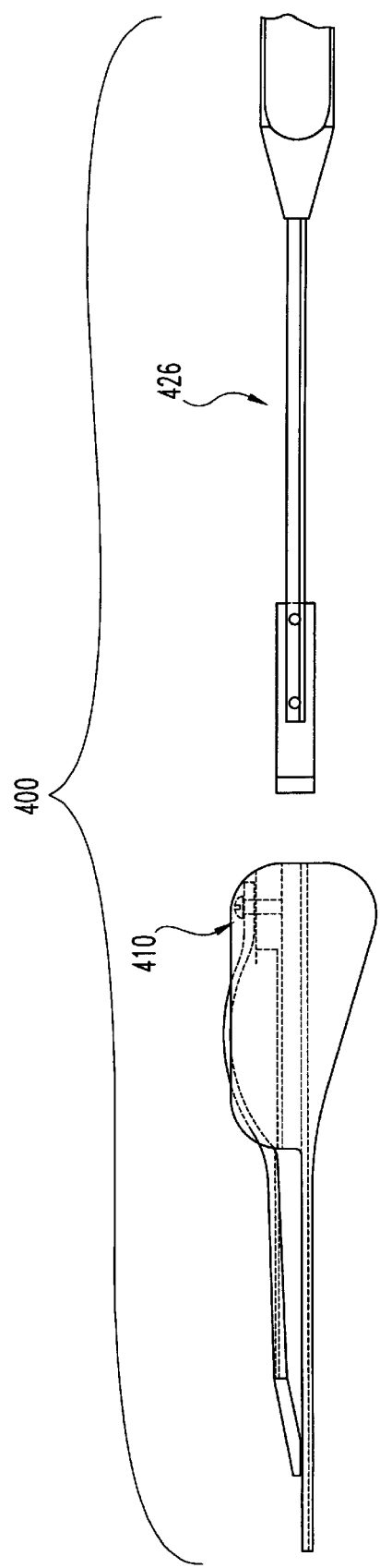
FIG. 22 is a side view of a carpal tunnel device in accordance with one embodiment of the present inventions.
Figure 23:
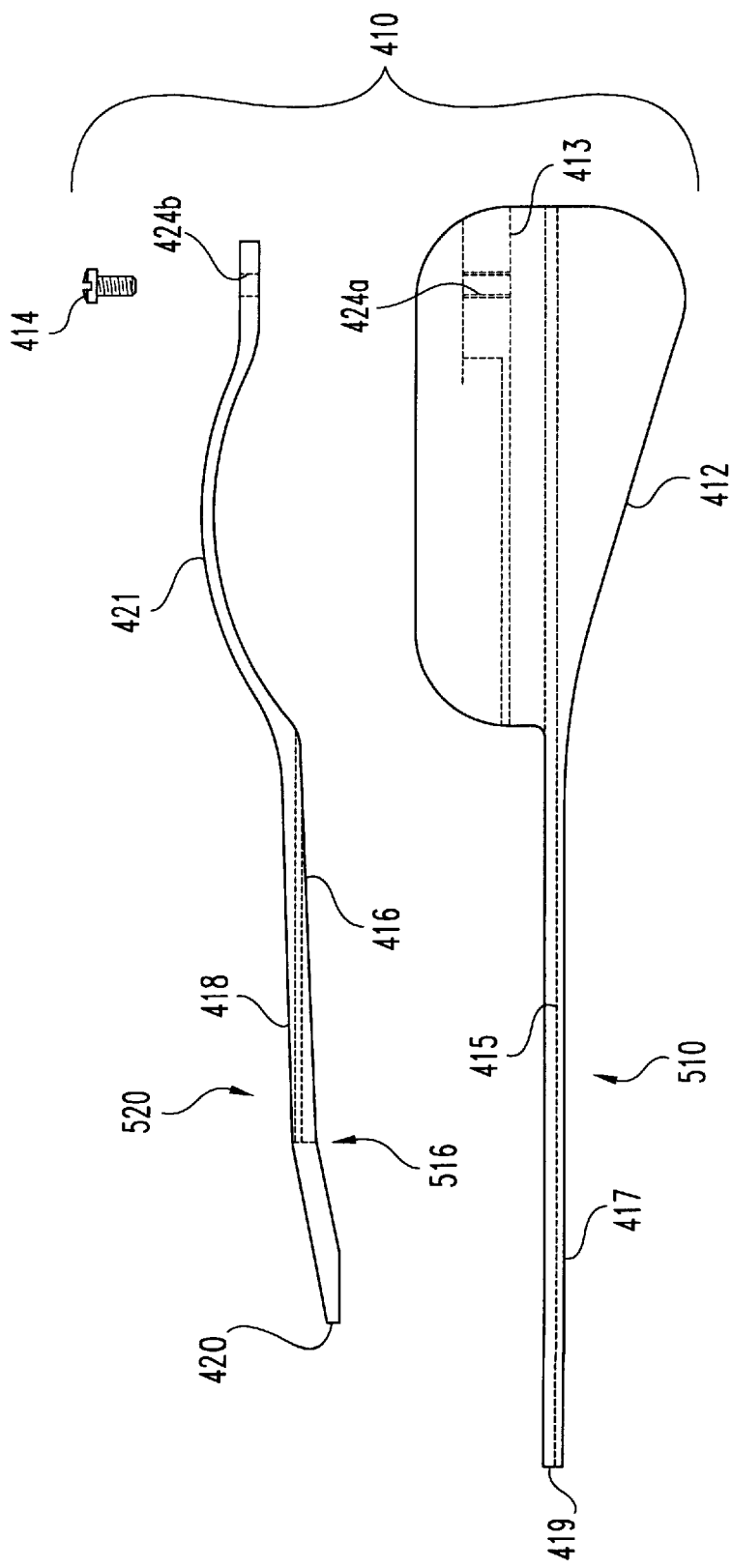
FIG. 23 is an exploded side view of a carpal ligament capture clip of the carpal tunnel device of FIG. 22.

Referring now to FIG. 23, there is shown an exploded view of the carpal ligament capture clip 410 of FIG. 22. The carpal ligament capture clip 410 comprises a guide portion 510 and a capture arm 520. Although shown as a two piece construction comprising the guide portion 510 and the capture arm 520, the carpal ligament capture clip 410 may be made of as a single piece device including those parts, if desired. Like the guide portions of the previous embodiments, the guide portion 510 of the carpal ligament capture clip 410 includes a body portion 412 and a lower skid portion 417. However, unlike the above described embodiments, the guide portion 510 of the present embodiment does not include a distinct handle. In use, the body portion 412 is grasped between the thumb and forefinger. The body portion 412 may optionally be enlarged, as shown in FIGS. 22 and 23, so as to be more easily held during use.

Figure 24A:
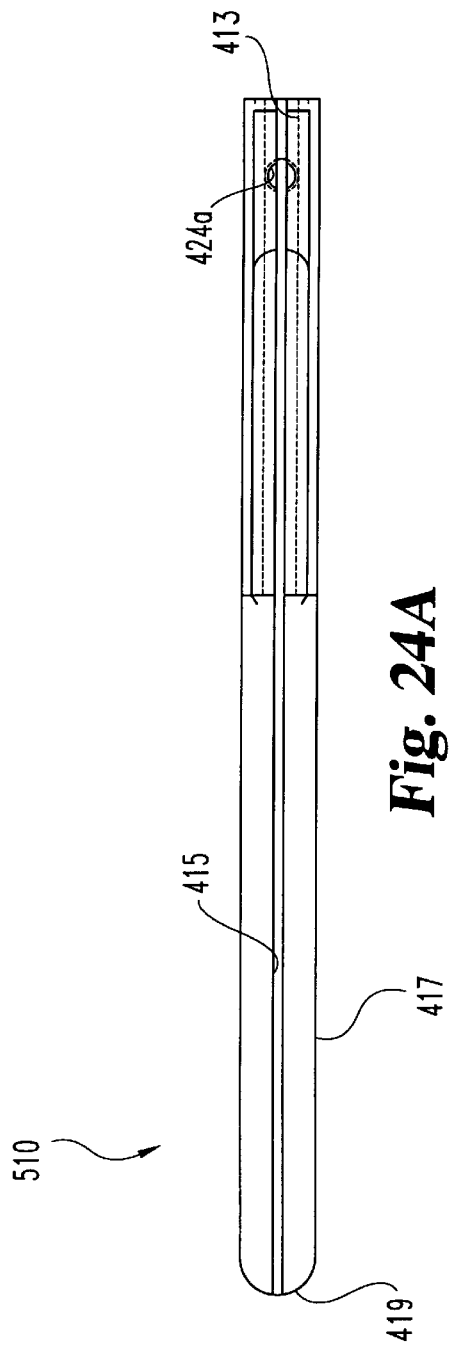
FIG. 24A is a top view of the body portion of the carpal ligament capture clip of FIG. 23.
Figure 24B:
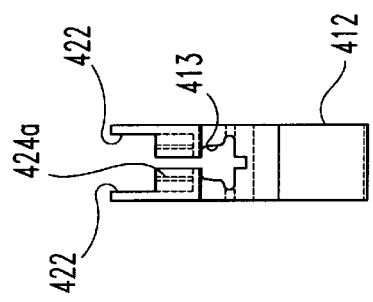
FIG. 24B is an end view of the body portion of FIG. 24A.

Referring to FIGS. 23, 24A and 24B, The body portion 412 includes a central guide channel 413 therethrough to receive the blade and shaft of knife 426 (or any knife desired). The cross-sectional shape of central guide channel 413 is preferably adapted to closely fit the cross-sectional shape of the shaft of the knife 426, and additionally provides clearance in the body portion 412 for the blade. In the example of FIGS. 26A–26D, the cross-sectional shape of knife 26 is "T" or bell shaped. If desired, other shaft cross-sectional geometries may be used.

The lower skid 417 of the guide portion 510 includes a blunted tip 419, and a lower guide channel 415 aligned with the central guide channel 413 of the body portion 412. The lower guide channel 415 may, optionally extend the entire length of the lower skid 417, as shown, or may, alternatively extend for only a portion of the lower skid. Depthwise, the lower guide channel 415 extends through only a portion of the skid, thus the blade of the knife 426 is not exposed to tissue below the lower skid 417. The lower guide channel 415 can have a cross-sectional shape adapted to receive the lower portion of the blade or the lower portion of the blade along with a portion of the knife shaft, if desired. FIG. 24A is a top view of the guide portion. FIG. 24B is an end view of the guide portion of FIG. 24A. As can be seen more particularly in FIG. 24A, the body portion 412 includes a threaded hole 424a for engaging the screw 414 of FIG. 23. Screw 414 may be replaced by any appropriate type of fastener, rivet, bolt, etc., or may be omitted entirely and the upper skid may be soldered or welded to the body 412.

Figure 25A:
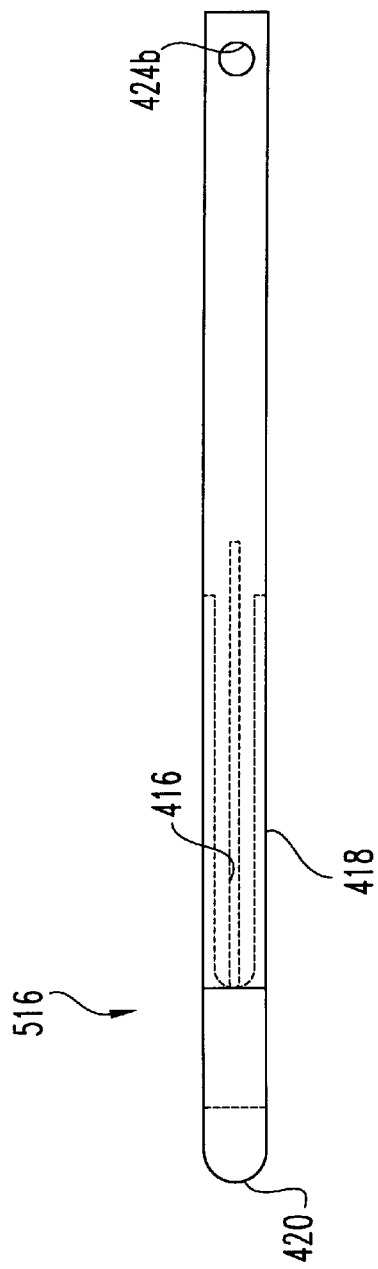
FIG. 25A is a top view of the capture portion of the carpal ligament capture clip of FIG. 23.
Figure 25B:
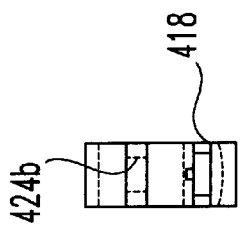
FIG. 25B is an end view of the capture portion of FIG. 25A.
Figure 27:
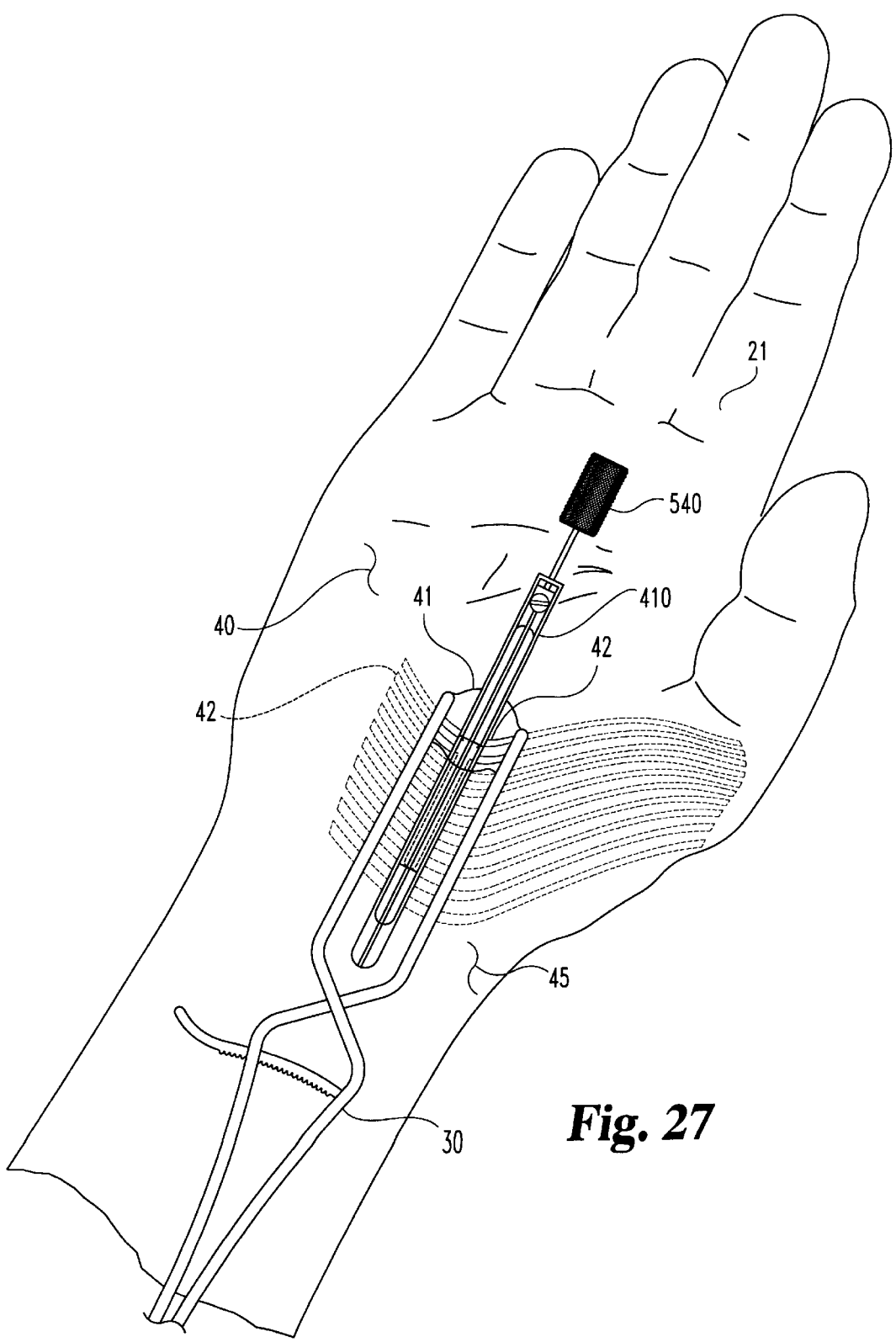
FIGS. 27 and 28 are views of the palmar side of a patient's hand and wrist showing the use of the device of FIG. 22 in selected steps of a carpal tunnel release surgery according to one technique of the present invention.

Referring now to FIGS. 23, 25A and 25B, FIG. 25A is a top view of the capture arm 520 of the carpal ligament capture clip 410. The capture arm 520 includes an upper skid 418. Upper skid 418 includes a blunt tip 420 and an upper guide channel 416 aligned with the central guide channel 413 of the body 412. As with the lower guide channel 415 of the guide portion 510, the upper guide channel 416 of the upper skid 418 may be adapted to have the desired cross-sectional shape of the upper portion of the blade or of the blade and a portion of the shaft of the knife, so as to align the knife when slid through the passage of central guide channel 413 and along the extended guide channel formed in the upper and lower skids. Depthwise, the upper guide channel 416 extends through only a portion of the skid, thus the blade of the knife 426 is not exposed to tissue above the upper skid 418. The total combined length of the central guide channel 413 and the upper guide channel 416 should be greater than at least 3 cm, to ensure that the entire carpal ligament is cut prior to the knife blade encountering the end of the upper guide channel 416.

The capture arm 520 additionally includes a hole 424b therethrough to allow screw 414 to pass. Shoulders 422 (FIG. 24B) are used to prevent the capture arm 520 from becoming skewed, and thus unaligned with the central guide channel 413, when the capture arm 520 is mounted to the guide body 510. Shoulders 422 may be omitted, if desired, and would be unnecessary if the capture arm 520 and the guide body 510 were a single piece device, or were welded or permanently attached together in some fashion.

As described above in connection with other embodiments, optionally the lower skid 417 of the carpal ligament capture clip 410 is designed to extend beyond the tip 420 of the upper skid 418 to permit visual confirmation of the correct positioning of the carpal ligament capture clip 410 through direct observation in the wound. Additionally, the opposing inside surfaces of skids 417 and 418 are relatively smooth to permit the carpal ligament to slide between the two skids when the device is introduced into the palm.

If desired to aid in conforming to the changing width of the carpal ligament, the upper skid 418 may be chosen to be about 2 mm thicker at the distal end of the upper guide channel 416 (proximal to tip 420, and to the wrist end of the carpal ligament when in use), than at the proximal end of the upper guide channel 416 (proximal to the palmar portion of the carpal ligament when in use). Thus the clip will closely adapt to the narrowing width of the transverse carpal ligament as it is passed from the palm to the wrist. At rest, there may be a slight separation between the tips 419 and 420 of the lower and upper skids 417 and 418 to permit the transverse carpal ligament to be initially straddled by the upper and lower skids when first placing the device. Preferably, the carpal ligament capture clip 410 is normally spring biased closed at tips 419 and 420, leaving no gap or a very minimal gap between the tips of the skids. This is designed to keep tissue, other than the carpal ligament, from getting in between the skids during insertion. As shown in FIG. 29, an obturator 540 or other tool may be used to bias the tips 419 and 420 apart during insertion. Because of the close conformance of the instrument to the ligament, there should be no possibility of extraneous soft tissue entering between the skids where they might be damaged during knife passage.

Referring now to FIGS. 26A–26D, there is shown one possible embodiment of a knife for use with the present invention. Knife 426 includes, a shaft 428 and a blade 429. Optionally, knife 426 additionally includes a handle 427. The handle 427 may be contoured, as shown or in any other desired manner, to provide for easy gripping of the tool. Connected to the handle 427 is the proximal end of the shaft 428. The shaft 428 of the knife 426, of the present embodiment, has a cross-sectional shape of a "T", as can be seen in FIGS. 26C and 26D. As noted above, other geometrical cross-sectional shapes for the shaft may be used, as desired. At the distal end of the shaft 428 is the blade 429.

In the present embodiment, the height of blade 429 was chosen to be greater than the diameter of the shaft 428, such that blade 429 extends above and below the shaft an equal amount, as shown in FIGS. 26A, 26C and 26D. The distal end of blade 429 includes the cutting edge 429a. As noted above, the cross-sectional shape of central guide channel 413 may be sized to conform to the cross-sectional shape of the shaft, while permitting additional clearance in the top and bottom portions of the central guide channel for the blade 429.

Additionally, as the blade 429 and shaft 428 extend into the extended guide channels of the skids, in use, a progressive amount of the knife blade will be covered by the upper skid, thus the knife will only cut the narrowing ligament with no risk of damage to adjacent tissues. In the present embodiment, at a point 516 before the distal tip 420 of the upper skid 418, the upper guide channel 416 ends. In one particular embodiment where the upper skid is about 2.2 inches in length and the lower skid was chosen to be about 2.5 inches, the guide channel in the upper skid ends more than 0.5 inch from the tip of the upper skid. This serves to stop the passage of the knife blade at the termination of the upper guide channel 416, thus not permitting the knife blade 429 to exit the clip, or even to travel the full length of the bottom skid 417. Alternatively, a stop, such as stop 228 of FIG. 8A may be used to prevent the knife blade 429 from exiting the upper guide channel 416, if the upper guide channel were designed to extend the entire length of the upper skid.

Operative Procedure

Figure 9:
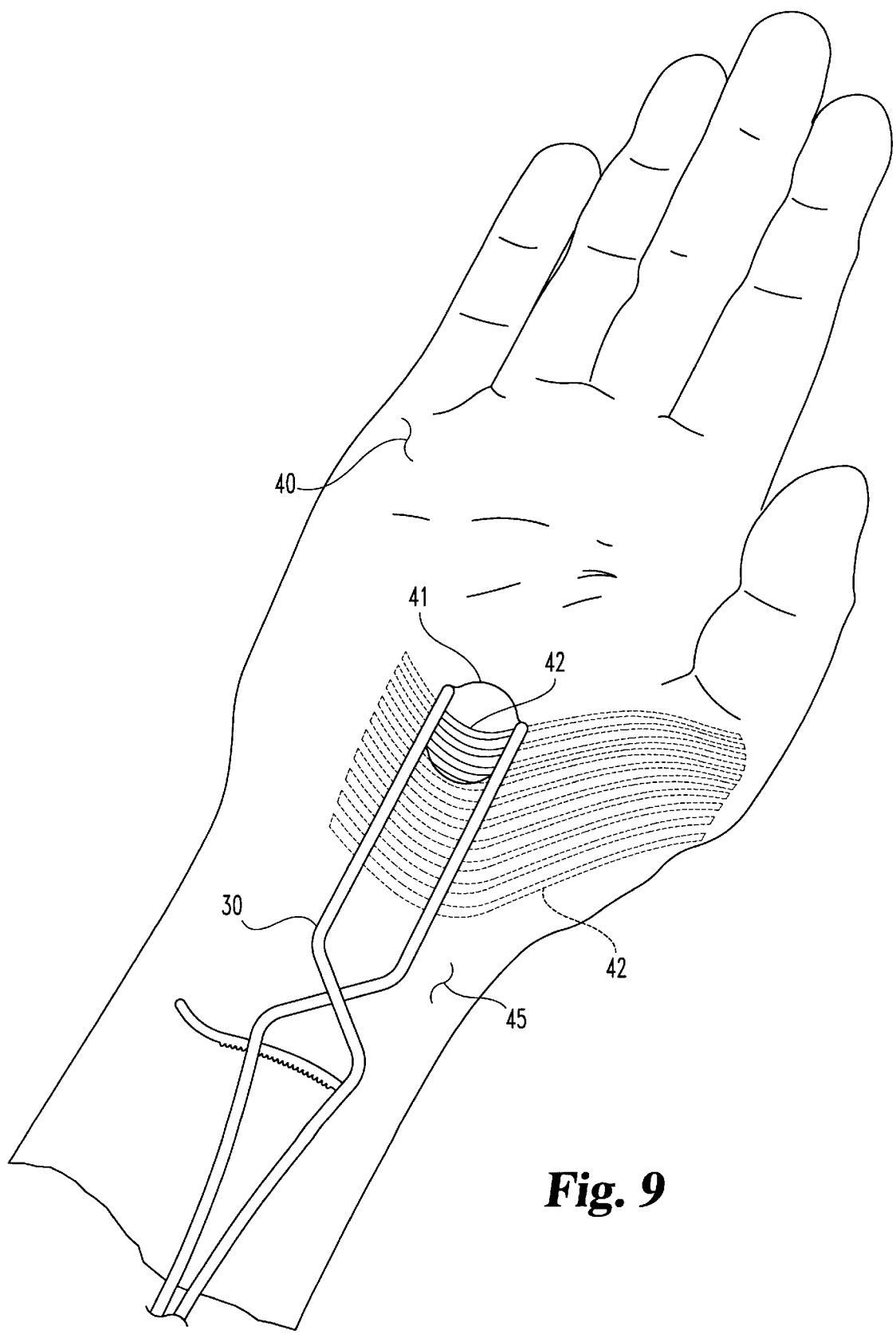
FIGS. 9–11 and 13–14 are views of the palmar side of a patient's hand and wrist showing serially the carpal tunnel release surgery according to the technique of the present invention.

Referring to FIGS. 9–14 and 27–29, the patient is brought to an outpatient operating room where approximately 10 cc of local anesthetic agent are infiltrated under the proximal palmar skin, across the wrist crease and into the sub fascial wrist compartment. Additional anesthetic material is also infiltrated directly into the carpal tunnel. Under tourniquet control, a 1–2 cm incision 41 is made between the thenar and hypothenar musculature on the palmar side 40 of the patient's hand as shown in FIG. 9. Sharp dissection is carried down to provide exposure, and a small Holzheimer or equivalent self-retaining retractor instrument 30 is usually repositioned several times as increasing depth of the incision is created by sharp and blunt dissection. A surgical sponge (not shown) may also be used to further clarify the level of dissection until the distal portion of the deep transverse carpal ligament 42 is clearly visualized through the incision, and all overhanging adipose tissue retracted.

Figure 10:
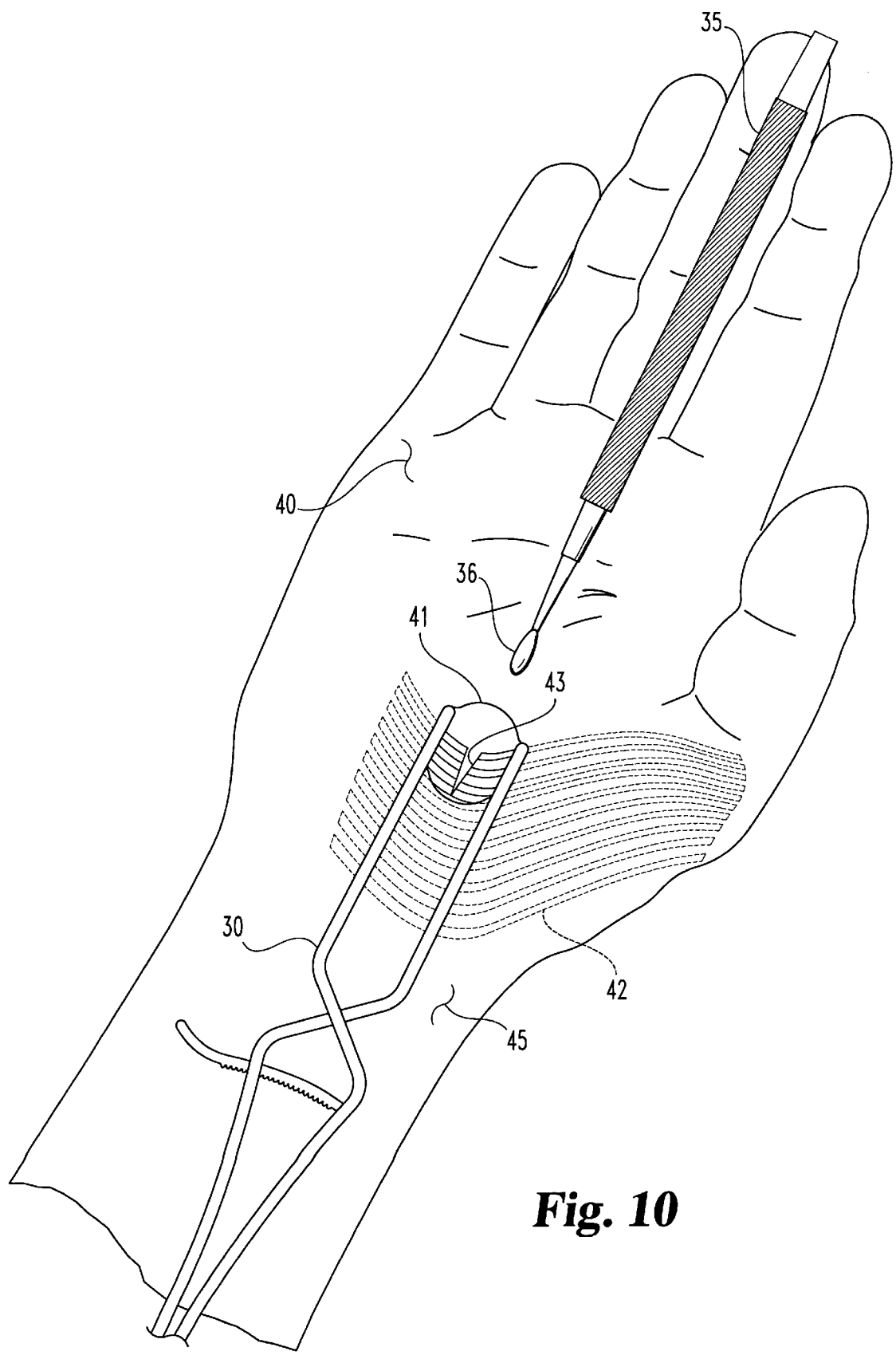

Referring now to FIG. 10, in the preferred method, the distal 1 to 1½ cm portion 43 of the ligament is then sharply divided, exposing the contents of the carpal vault. The curved end 36 of a Freer elevator 35 or the curved end of a probe, (such as the curved end 120 of probe 110 of U.S. Pat. No. 5,507,800, that patent incorporated by reference herein) is then placed beneath the partially divided ligament and gently passed proximally toward the patient's wrist 45 for 3–4 cm to separate the contents of the carpal tunnel from the ligament 42. Similarly, the Freer elevator or probe may be passed on the palmar surface of ligament 42 to separate any fascial connections.

Figure 11:
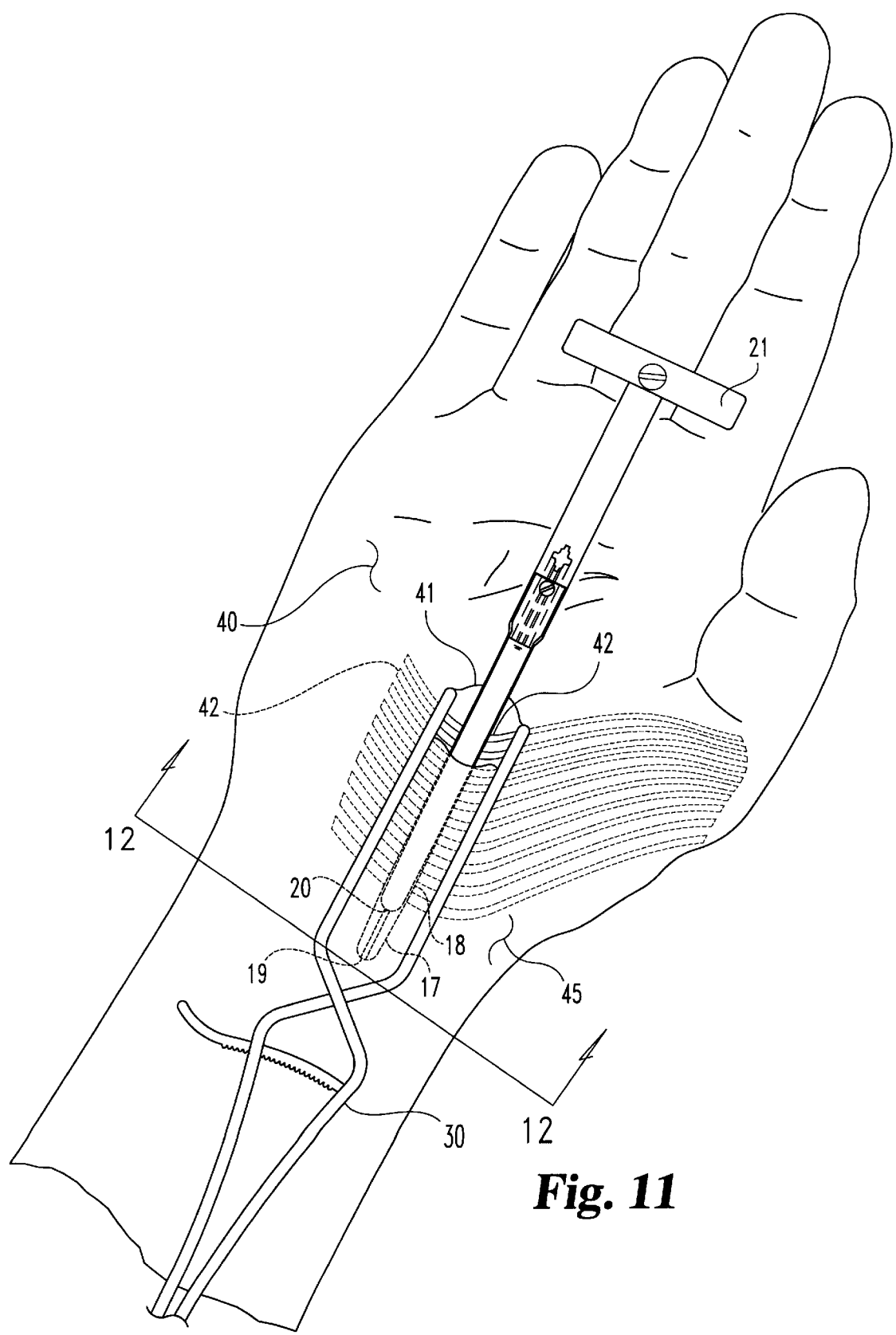

Next, division of the carpal ligament may be accomplished using the present inventions. For example, any of the above described carpal tunnel devices 100, 200, 300 and 400 of FIGS. 1, 6A, 15 and 22 may be used. For purposes of example only, the carpal tunnel device 100 is shown in use in FIGS. 11, 12, and 13. Referring to FIG. 11, the carpal ligament capture clip 10 (or 210 of carpal tunnel device 200, 310 of 300, 410 of 400), is inserted into the wound with exposure being maintained by the Holzheimer self-retaining retractor 30. A small right-angle retractor (not shown) is preferably placed on the proximal aspect of the wound so that the leading skid 17 of capture clip 10 (or 217 of capture clip 210; 317 of capture clip 310, 417 of capture clip 410) can be accurately placed beneath the ligament 42 under direct vision, such that both tips 19 and 20 of the upper and lower skids (or 219 and 220; 319 and 320. 419 and 420) extend beyond the ligament 42.

Optionally, prior to insertion of the carpal ligament capture clip 10 (or 210; 410), if the tips of the upper and lower skids are normally biased closed, an obturator or similar device may be used to bias them open during insertion. For example, referring to FIG. 29, there is shown the carpal ligament capture clip 412, the tips 419 and 420 of which are normally biased closed when at rest. Prior to insertion, an obturator 540 has been inserted into the device 410 (or, if desired, 10 or 210) to separate the upper and lower skids. As the tips are normally biased closed, the use of an obturator to separate the skids helps insure that the clip contacts and places pressure on the ligament during insertion. Additionally, use of an obturator or like device permits the user to limit the opening between the tips of the skids to about the diameter of the obturator shaft. In one particular embodiment, the obturator or like device is used to limit the opening between the skids to about 3 mm. In use, the ligament pushes the obturator or like device out of the clip, up to the central guide channel through the guide body. Preferably, the tip of the obturator or like device does not extend past the tip 420 (or 20; 220) of the upper skid. Optionally, if desired, the cross-sectional shape of the obturator shaft may correspond to the cross-sectional shape of the central guide channel through the guide body.

Figure 28:
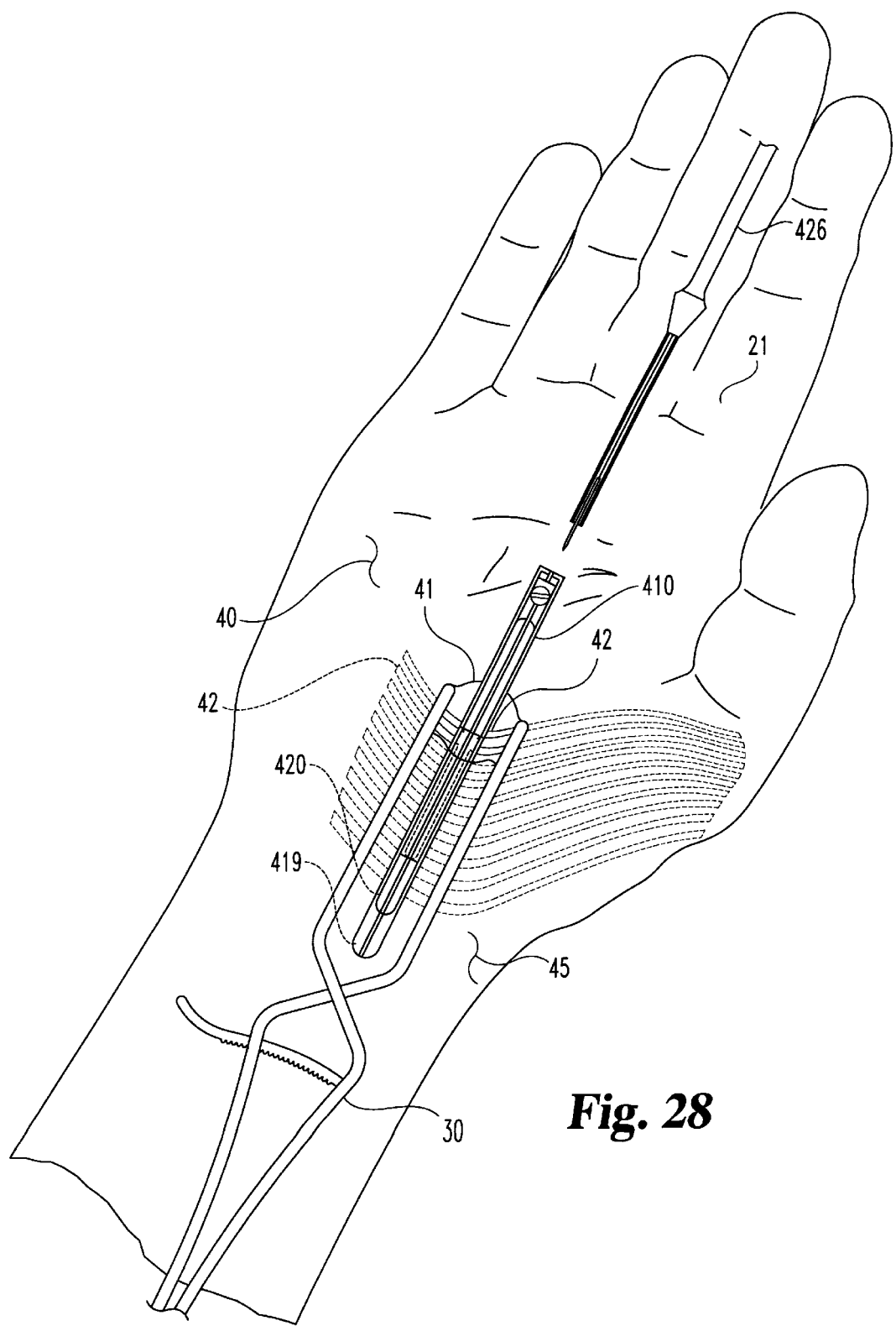

Referring back to FIG. 11, the handle 11 of the capture device 10 (and 211 of capture device 210) is contoured downward, towards the palm, and, once in place, will not impair visualization of the entry slot for the cutting knife. If desired, the handle 311 of the capture clip 310 may be contoured downward, or may be designed as shown, having a sufficiently low profile that, while flat and in the same plane as the guide body 370, does not impair visualization of the entry slot for the cutting knife. Alternatively the device may have no handle, as shown in FIG. 28 in connection with the capture clip 410, by way of example.

Figure 12:
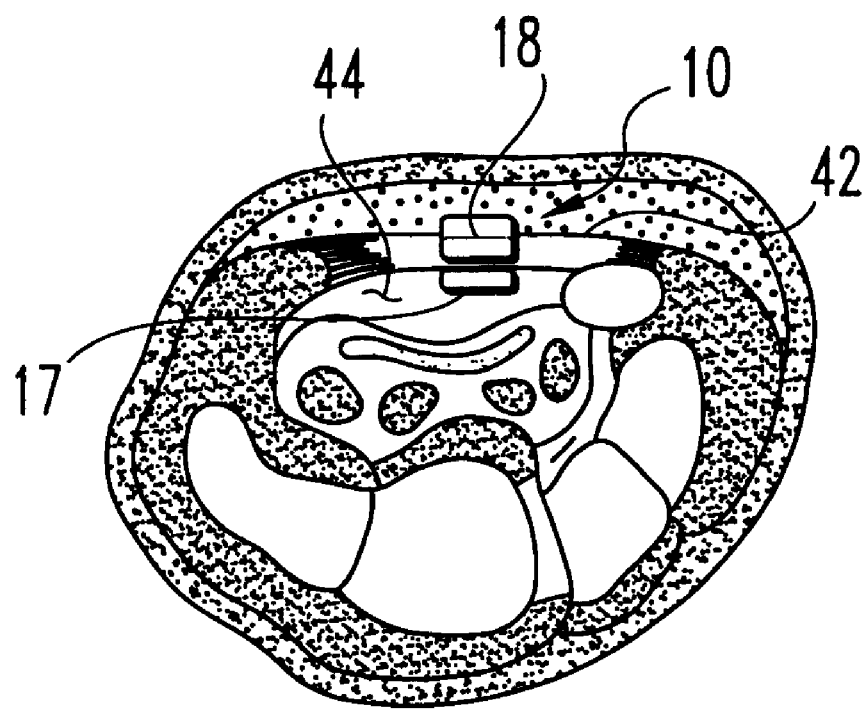
FIG. 12 is a cross-section through the patient's wrist at a midpoint in the surgery looking in the direction of arrows 12—12 of FIG. 11.

As the capture clip 10 (or 210; 310, 410) is advanced in the wound, the carpal ligament is bounded on the top and bottom sides by the upper and lower skids as shown in FIGS. 11 and 12. For the embodiments of FIGS. 1 and 6A, the natural spring separation of the skids attached to the capture clip body, as described herein, permits the opening between the skids to normally conform to the carpal ligament as the clip is slid over the ligament. For example, to assure compliance of both skids to the ligament as the instrument is passed from the palmar end of the ligament to the wrist end, due to the natural slight spring separation, the distance between the upper and lower skids will initially be wider but will progressively narrow and continuously grasp the transverse carpal ligament as it becomes thinner.

For the embodiment of FIG. 15, the physician will grip the device and apply a force to the capture arm handle 321 in the direction of arrow A1 to cause the upper and lower skids to separate a set amount predetermined by the shoulders 327, as described herein. In that embodiment, the clip will be slid over the distal edge of the ligament while the skids are separated. As above, a visual determination is made to detect that the ligament 42 is completely encompassed between the upper skid 318 and the lower skid 317, with the upper skid tip 320 visible. After the capture clip is correctly positioned, the force on the capture arm handle 321 is released and the spring element causes the capture clip arm 380 to return to its normally biased closed position, forcing the skids to closely conform to the carpal ligament 42 entrapped there between.

Once fully inserted, the capture clip 10 (or 210; 310, 410) will be contiguous with the ligament throughout the ligaments 3.5 to 4 cm course, and its central guide slot will be prepared to accept the cutting knife 26 (or 226, 426).

Figure 13:
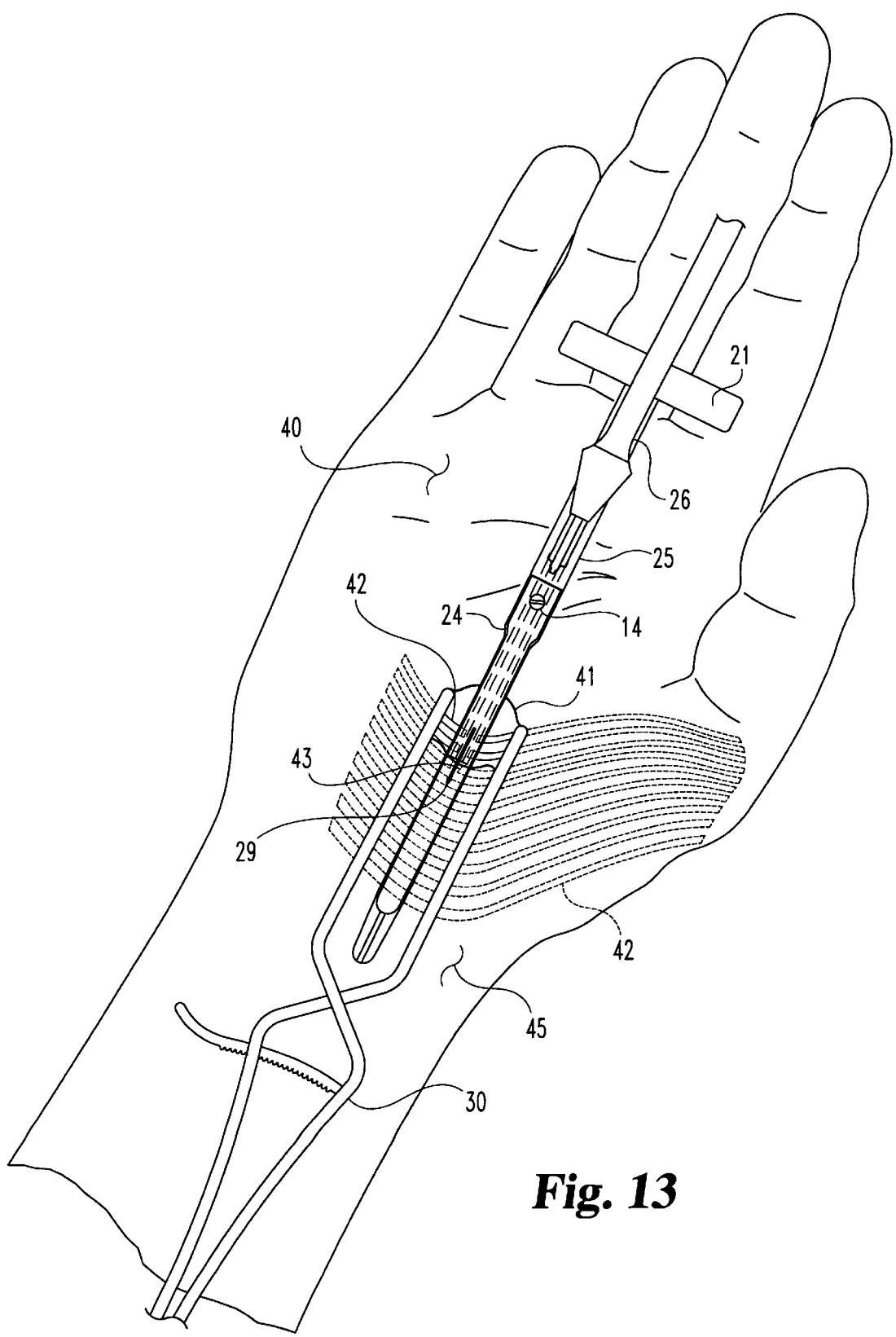

Next, as shown in FIG. 13, the knife 26 is introduced into the central guide channel 13 (or 213; 313, 413) and advanced until the edge 29a (or 229a, 429a) of blade 29 (or 229, 429) contacts the carpal ligament 42. The knife 26 (or 226, 426) is further advanced approximately 3 to 4 cm, until the ligament 42 is bisected and the leading edge 29a of blade 29 (or 229a of 229, 429a of 429) encounters the end of the channel in the upper skid. If a knife having a stop is used, such as stop 228 in FIG. 8A, the passage of the knife will stop when the stop 228 abuts the body of the capture clip.

Figure 14:
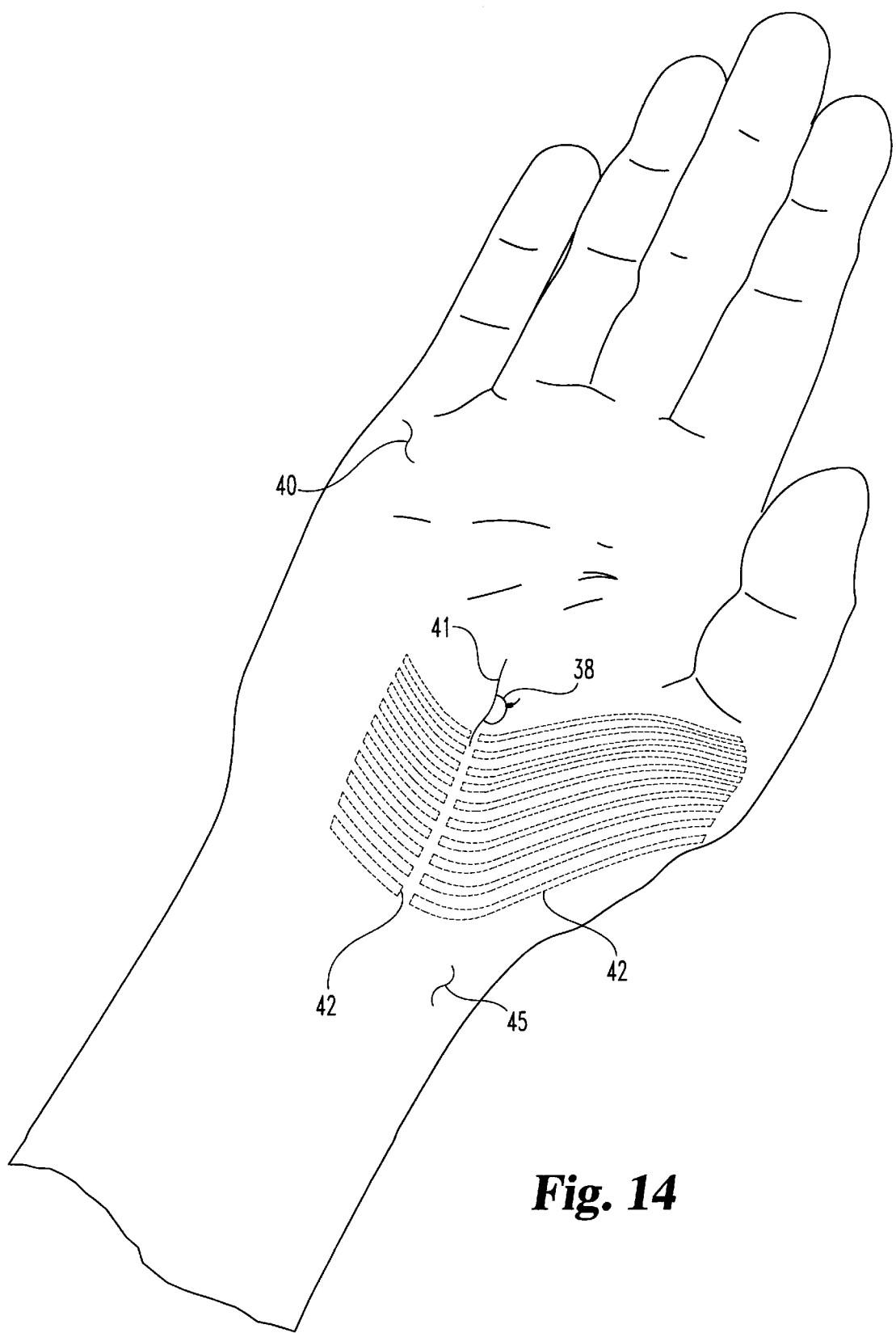

At this point the capture clip and knife are withdrawn from the small wound allowing the surgeon to directly view the carpal tunnel 44 (of FIG. 12) and confirm the gapping between the radial and ulnar edges of the divided ligament; this allows the surgeon to confirm that the ligament 42 has been completely divided and the median nerve decompressed. Gently teasing the nerve to be sure that it is soft and nonadherent may then be carried out and a limited inspection of the carpal vault for any underlying lesions may also be done. After the wound has been irrigated, one or two sutures 38 are then used to close incision 41 as shown in FIG. 14. A small compressive dressing (not shown) is then applied from the distal forearm to the mid-palm, and the patient is encouraged to vigorously move his or her fingers. After the surgery, the patient generally returns to the office in 10–14 days for suture removal.

While the inventions have been illustrated and described in detail in the drawings and foregoing description, the same is to be considered as illustrative and not restrictive in character, it being understood that only the preferred embodiment has been shown and described and that all changes and modifications that come within the spirit of the inventions are desired to be protected.

For example, although the preferred embodiments above have been described as including upper and lower guide channels in the skids, in addition to the central guide channel through the body of the capture clip, it is contemplated that one or both of the upper and/or lower guide channels may be omitted, if desired. Similarly, although it has been described herein that it is preferable to adapt the central guide channel of the inventions to closely conform to the shaft and/or blade of the knife, optionally, the central guide channel need not closely conform, but may instead merely be a passage through the body portion of the device.

Additionally, the embodiments described herein as being two piece constructions may be manufactured as a single piece, if desired. Conversely, the embodiment described herein as a single piece construction may be constructed of multiple pieces without departing from the spirit of the invention.

Further, although it has been stated herein that a knife may include a blade and a shaft, it is understood that for purposes of this invention the blade may be an extension of the shaft and/or integrally formed with the shaft, such as in the embodiment shown in FIGS. 8A–8C.

What is claimed is:

1. A method of performing carpal tunnel release surgery, comprising the steps of:
   making an incision adjacent one of the distal edge and proximal edge of the transverse carpal ligament;
   retracting the incision until the transverse carpal ligament is visible;
      providing a carpal ligament capture clip, said capture clip comprising a guide body including a central guide channel therethrough, said guide body including a proximal and a distal end, said capture clip further including an upper skid, located at the distal end of said guide body and a lower skid located at the distal end of said guide body opposite and facing said upper skid;
      positioning a portion of said carpal ligament capture clip in the incision so that the transverse carpal ligament is enveloped between said upper and lower skids;
      providing a knife adapted to be inserted into and slideably received through said central guide channel;
      inserting said knife into said central guide channel at said proximal end of said guide body;
      advancing said knife through said central guide channel between said upper and lower skids until the transverse carpal ligament is completely divided; and
      withdrawing said capture clip and said knife from the patient.

2. The method of claim 1, wherein at least one of said upper skid and said lower skid includes a guide channel aligned with at least a portion of said distal end of said central guide channel.

3. The method of claim 1, wherein said providing step includes providing a carpal ligament capture clip wherein at least a portion of one of said upper skid and said lower skid is flexible to permit said upper skid to conform to the changing width of the transverse carpal ligament during said advancing step.

4. The method of claim 1, wherein said providing step includes providing a carpal ligament capture clip, wherein said upper skid is normally spring biased towards said lower skid and wherein said positioning step is performed while said upper skid is manually forced away from said lower skid.

5. The method of claim 1, wherein said providing step includes providing a carpal ligament capture clip, wherein said upper skid is journaled to said guide body by a shaft at a pivot point, said upper skid additionally including an upper skid handle portion connected to said upper skid at said pivot point, said capture clip additionally including a spring, wherein said upper skid is normally spring biased towards said lower skid by said spring, and wherein said method additionally comprises the steps of applying a force to said upper skid handle in a direction substantially perpendicular to said guide body to lever said upper skid away from said lower skid prior to said positioning step.

6. The method of claim 5, wherein at least one of said upper skid and said lower skid includes a guide channel aligned with at least a portion of said distal end of said central guide channel.

7. A carpal tunnel device for dividing the transverse carpal ligament, comprising:
   a carpal tunnel capture clip, including:
      a body portion, having a proximal end and a distal end and defining a central guide channel therethrough,
      a lower skid extending from the distal end of said body portion and an upper skid extending from said distal end of said body portion generally parallel to said lower skid, and
   a knife, adapted to be slideably received through said central guide channel and between said upper skid and said lower skid.

8. The carpal tunnel device of claim 7, wherein said lower skid extends beyond the distal tip of said upper skid.

9. The carpal tunnel device of claim 7, wherein at least one of said upper skid and said lower skid is spring biased toward the other one of said upper skid and said lower skid.

10. The carpal tunnel device of claim 7, wherein said upper skid thickness is non-uniform along at least a portion of the length of said upper skid.

11. The carpal tunnel device of claim 7, wherein at least one of said upper skid and said lower skid includes a guide channel therein, said guide channel being aligned with at least a portion of said central guide channel.

12. The carpal tunnel device of claim 7, wherein said upper skid defines an upper guide channel having an end point spaced from the distal tip of said upper skid.

13. The carpal tunnel device of claim 12, wherein the end point of said upper guide channel is at least 3 cm from the distal end of said central guide channel.

14. A carpal tunnel device for dividing the transverse carpal ligament, comprising:
   a carpal tunnel capture clip, comprising:
      a guide body, including:
         a guide handle, having a proximal end and a distal end,
         a body portion, having a proximal end and a distal end, said proximal end connected to the distal end of said guide handle, said body portion including a central guide channel therethrough,
         a lower skid extending from the distal end of said body portion,
      a capture arm, comprising:
         a capture arm handle,
         an upper skid extending from the distal end of said capture arm handle,
      a pivot, connected between said guide body and said capture arm, such that said capture arm pivots with respect to said guide body, and wherein the inner surface of said upper skid is connected proximal to and facing the inner surface of said lower skid, and wherein said capture arm handle is disposed above at least a portion of said guide handle, said pivot located between said upper skid and said capture arm handle,
      wherein when a force is applied to said capture arm handle in a direction towards said guide handle, said capture arm pivots at said pivot, and lifts said portion of said upper skid off said lower skid, thus separating the distal end of said upper skid from said lower skid, and
   a knife, adapted to be inserted into and slideably received through said central guide channel.

15. The carpal tunnel device of claim 14, wherein said carpal tunnel capture clip additionally includes a spring connected between said guide body and said capture arm handle to normally bias a portion of the distal end of said upper skid into contact with said lower skid.

16. The carpal tunnel device of claim 15, wherein said guide body includes shoulders through which said pivot passes, said shoulders providing a pivot arm between said guide body and said capture arm.

17. The carpal tunnel device of claim 16, wherein said capture arm handle includes at least one shoulder stop limiter aligned with said guide body, such that when a force is applied to said capture arm handle in the direction of said guide handle, said shoulder abuts said guide body to limit the amount of separation between said upper skid and said lower skid.

18. The carpal tunnel device of claim 15, wherein said upper guide channel ends at an end point prior to the distal tip of said upper skid, and wherein said upper skid is thickest near to said end point.

19. The carpal tunnel device of claim 15, wherein the end point is proximal to the distal tip of said upper skid, and wherein the passing of said blade is impeded beyond the end point.

20. The carpal tunnel device of claim 15, wherein the knife includes a blade and a shaft extending from said blade, and wherein the cross-sectional geometry of said central guide channel closely conforms to the cross-sectional geometry of said shaft and said blade.

21. For use in a carpal tunnel release system with a carpal tunnel capture clip having a body portion with a proximal end and a distal end and a central guide channel therethrough, a lower skid extending from the distal end of said body portion including a lower guide channel aligned with the central guide channel and an upper skid including an upper guide channel aligned with the central guide channel, the upper skid extending from said distal end of said body portion generally parallel to said lower skid, a knife comprising:

a shaft, at least a portion of which is slidably receivable through the central guide channel, said shaft having a proximal end and a distal end; and a blade portion located at the distal end of said shaft, said blade portion including a top channel riding portion, a bottom channel riding portion and a cutting edge bounded therebetween, said top and bottom channel riding portions configured to be slidably received in the upper and lower guide channels of the upper and lower skids when said knife is passed through the central guide channel; and wherein a cutting edge plane defined through said cutting edge, said top channel riding portion and said bottom channel portion is generally perpendicular to a skid plane parallel to a plane defined through the inner surfaces of the upper and lower skids when the top and bottom channel riding portions ride in the upper and lower guide channels.

22. The knife of claim 21 wherein the height of said blade along the cutting edge plane is the same as the height of said shaft.

23. The knife of claim 21 wherein the height of said blade along the cutting edge plane is greater than the height of said shaft.

24. The knife of claim 23 wherein the height of the blade along the cutting edge plane is sized to pass through a central guide channel about 4 mm in height.

25. The knife of claim 24 wherein the cross-sectional shape of the central guide channel is adapted to closely fit the cross-sectional shape of said shaft while providing clearance for said blade.

26. The knife of claim 25 wherein said cross-sectional shape of said shaft is "T" or bell shaped.

27. The knife of claim 25 wherein said cross-sectional shape of said shaft is rectangular.

28. The knife of claim 21 wherein said blade is integrally formed with said shaft.

29. The knife of claim 28 wherein said knife additionally includes a handle connected to the proximal end of said shaft.

\* \* \* \* \*